United States Patent [19]

Hornback et al.

[11] Patent Number: 5,099,015
[45] Date of Patent: Mar. 24, 1992

[54] TRIFLUOROMETHYL 1-CARBA(1-DETHIA)CEPHEMS

[75] Inventors: William J. Hornback; John E. Munroe, both of Indianapolis, Ind.

[73] Assignee: Eli Lilly and Company, Indianapolis, Ind.

[21] Appl. No.: 639,475

[22] Filed: Jan. 10, 1991

[51] Int. Cl.$^5$ .............. C07D 463/00; C07F 7/22; C07B 39/00; C07B 37/04
[52] U.S. Cl. ............................ 540/205; 540/201
[58] Field of Search ................................ 540/205

[56] References Cited

U.S. PATENT DOCUMENTS

| | | | |
|---|---|---|---|
| 4,327,225 | 4/1982 | Isogai | 560/205 |
| 4,347,367 | 8/1982 | Christensen | 540/350 |
| 4,673,737 | 6/1987 | Evans et al. | 540/205 |
| 4,980,348 | 12/1990 | Schmidt et al. | 514/210 |

FOREIGN PATENT DOCUMENTS

| | | |
|---|---|---|
| 14475 | 8/1980 | European Pat. Off. . |
| 25602 | 3/1981 | European Pat. Off. . |
| 27882 | 5/1981 | European Pat. Off. . |
| 75805 | 4/1983 | European Pat. Off. . |
| 154253 | 9/1985 | European Pat. Off. . |
| 301877 | 2/1989 | European Pat. Off. . |
| 326887 | 8/1989 | European Pat. Off. . |
| 890811 | 2/1989 | South Africa . |

OTHER PUBLICATIONS

Georgoulis, Bull. Chem. Soc. Fr. 1975, 607.
Meyers, Tetrahedron 27, 5979 (1971).
Collington, J. Org. Chem. 36, 3044 (1971).
Uyeo et al., *Synth. of 1-Carbacepham Derivatives*, Chem. Pharm. Bull., 28, (5), 1563 (1980).

*Primary Examiner*—Mark L. Berch
*Attorney, Agent, or Firm*—James J. Sales; Leroy Whitaker

[57] ABSTRACT

7-β-Acylamino-1-carba-(1-dethia)-3-trifluoromethyl-3-cephem-4-carboxylic acids and derivatives are provided as antibiotics. Pharmaceutical formulations comprising the antibiotics, intermediates, and a process for their preparation are also provided.

9 Claims, No Drawings

TRIFLUOROMETHYL 1-CARBA(1-DETHIA)CEPHEMS

BACKGROUND OF THE INVENTION

This invention relates to 1-carba(1-dethia)cephalosporin antibiotics, intermediates for the preparation thereof, to pharmaceutical formulations comprising the antibiotics, and to a method for the treatment of infectious diseases in man and other animals.

The 1-carba(1-dethia)cephalosporin antibiotics have the bicyclic ring system represented by the following formula wherein the numbering system is that commonly employed in the arbitrary cephem nomenclature system.

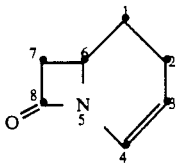

The 1-carba(1-dethia)cephalosporins are referred to herein for convenience as 1-carbacephalosporins or as 1-carba(1-dethia)-3-cephem-4-carboxylic acids or numbered derivatives thereof.

The preparation of 1-carbacephalosporins and C-3 substituted methyl derivatives thereof is taught broadly by Christensen et al., in U.S. Pat. No. 4,226,866. Hirata et al., in U.K. patent application No. 2041923, teach a method for preparing 3-H and 3-halo 1-carbacephalosporins, while Hatanaka et al., Tetrahedron Letters, 24, No. 44, pp. 4837-4838 (1983) teach a method for preparing a 3-hydroxy-(±)-1-carbacephalosporin.

Although many safe and potent antibiotics of the β-lactam class are known and used clinically, the research into this class continues in efforts to find antibiotics with improved efficacy, particularly against microorganisms insensitive or resistant to the known antibiotics.

SUMMARY OF THE INVENTION

The present invention provides 7β-acylamino-1-carba(dethia)-3-cephem-4-carboxylic acid antibiotics substituted at the 3-position with trifluoromethyl. The 7-position of these antibiotics is substituted by an acylamino moiety such as D-arylglycylamido or a heterocyclic-substituted oxminoacetylamino group. Also provided are pharmaceutical formulations comprising the antibiotics, intermediates, and processes for their preparation. Examples of such antibiotics include 7β-D-phenylglycylamido-1-carba(1-dethia)-3-trifluoromethyl-3-cephem-4-carboxylic acid, 7-β-D-p-hydroxyphenylglycylamido-1-carba(1-dethia)-3-trifluoromethyl-3-cephem-4-carboxylic acid, 7-β-D-m-methylsulfonylaminophenylglycylamido-1-carba(1-dethia)-3-trifluoromethyl3-cephem-4-carboxylic acid, and 7-β-[(2-aminothiazol-4-yl)-(Z)-methoximinoacetyl]amino-1-carba(1-dethia)-3-trifluoromethyl -3-cephem-4-carboxylic acid.

Detailed Description of the Invention

The present invention provides compounds of formula (1)

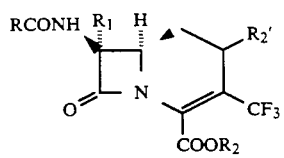

wherein
$R_1$ is hydrogen, $C_1$–$C_4$ alkoxy, $C_1$–$C_4$ alkylthio, or the formamido group $-NHCHO$;

$R_2$ is hydrogen or a carboxy-protecting group; $R_2'$ is hydrogen, hydroxy, $C_1$–$C_5$ alkyl, $C_1$–$C_5$ alkyl substituted by halogen, halogen, $C_1$–$C_5$ alkoxy, $C_1$–$C_5$ acyloxy, $C_1$–$C_5$ acyl, $C_1$–$C_5$ alkylthio, or nitrile; and R is the residue of a carboxylic acid, RCOOH; and when $R_2$ is hydrogen the pharmaceutically acceptable salts of the acids represented thereby.

The term "residue of a carboxylic acid" includes those 7-position side chains known in the cephalosporin and carbocephalosporin arts, and those 6-position side chains known in the penicillin art. Normally, these side chains are residues of $C_1$–$C_{20}$ carboxylic acids, and are exemplified when R is hydrogen; $C_1$–$C_6$ alkyl, $C_1$–$C_6$ alkyl substituted by cyano, carboxy, halogen, amino, $C_1$–$C_4$ alkoxy, $C_1$–$C_4$ alkylthio, trifluoromethyl, or trifluoromethylthio; naphthyl, a phenyl or substituted phenyl group of the formula

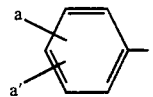

wherein a and a' independently are hydrogen, halogen, hydroxy, cyano, nitro, $C_1$–$C_4$ alkoxy, $C_1$–$C_4$ alkanoyloxy, $C_1$–$C_4$ alkyl, $C_1$–$C_4$ alkylthio, amino, $C_1$–$C_4$ alkanoylamino, $C_1$–$C_4$ alkylsulfonylamino, carboxy, carbamoyl, hydroxymethyl, aminomethyl, carboxymethyl, $C_1$–$C_4$ haloalkyl or $C_1$–$C_4$ perhaloalkyl; a group of the formula

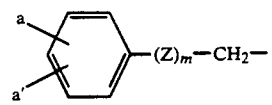

wherein a and a' have the same meanings as defined above, Z is O or S, and m is 0 or 1; an arylmethyl group of the formula

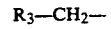

wherein $R_3$ is naphthyl, thienyl, furyl, benzothienyl, benzoaminothiazolyl, benzofuryl, pyridyl, 4-pyridylthio, pyrimidyl, pyridazinyl, indolyl, pyrazolyl, imidazolyl, triazolyl, tetrazolyl, oxazolyl, thiazolyl, oxadiazolyl, thiadiazolyl, and such aryl groups substituted by amino, hydroxy, cyano, nitro, halogen, $C_1$–$C_4$ alkyl, $C_1$–$C_4$ alkoxy, phenyl, substituted phenyl, or $C_1$–$C_4$ alkylsulfonylamino; a substituted methyl group of the formula

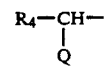

wherein R4 is cyclohex-1,4-dienyl, a phenyl or substituted phenyl of the formula

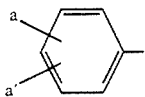

wherein a and a' are as defined above, or R4 is R3 as defined above, and Q is hydroxy, $C_1-C_4$ alkanoyloxy, carboxy, sulfo, amino, sulfoamino, or a substituted amino group of the formula

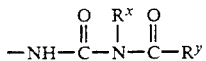

wherein $R^x$ is hydrogen or $C_1-C_3$ alkyl, $R^y$ is $C_1-C_4$ alkyl, furyl, thienyl, phenyl, halophenyl, nitrophenyl, styryl, halostyryl, nitrostyryl or a group of the formula

wherein $R^x$ has the same meanings as defined above and $R^z$ is hydrogen, $C_1-C_3$ alkylsulfonyl, $C_1-C_3$ alkyl, or $C_1-C_4$ alkanoyl; or Q is a substituted amino group of the formula

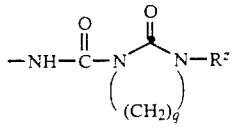

wherein $R^z$ has the same meaning as defined above, and q is 2 or 3; or Q is a substituted amino group of the formula

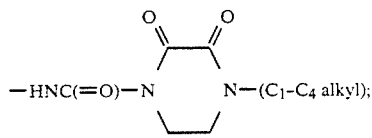

or Q is a benzamido group of the formula

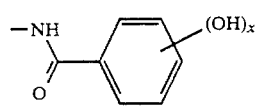

wherein X is 1 to 3;
or Q is a pyridone or hydroxy-substituted pyridonylcarbonylamino group of the formula

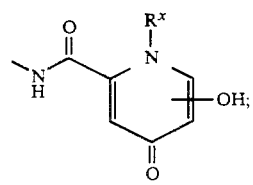

wherein $R^x$ is as defined above;
or Q is a pyridylcarbonylamino group of the formula

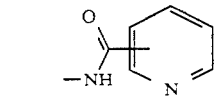

such group optionally substituted by $C_1-C_4$ alkyl, amino, carboxy, hydroxy or halogen; or Q is an imidazolyl or pyrazolyl group of the formula

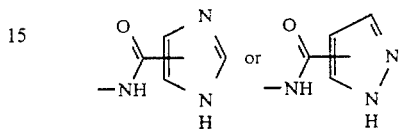

and such imidazolyl or pyrazolyl optionally substituted by $C_1-C_4$ alkyl, carboxy, amino, or halogen; or Q is a benzpyridazin-4-one group or tautomer thereof represented by the formula

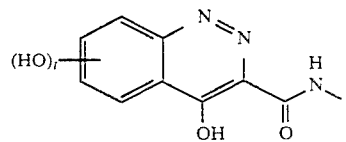

or

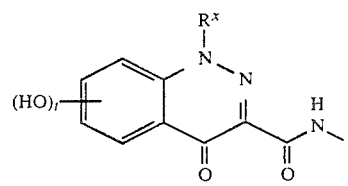

wherein $R^x$ is as defined above and t is 1 to 3; or Q is a benzpyranone group of the formula

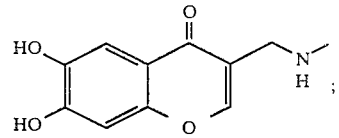

or R is a group of the formula

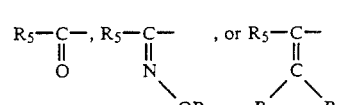

wherein $R_5$ is $R_3$ or $R_4$ as defined above, $R_{12}$ is hydrogen or halogen, and $R_6$ is hydrogen, $C_1-C_4$ alkyl, $C_1-C_4$ alkyl substituted by halogen, a carboxy-substituted alkyl or cycloalkyl group represented by the formula

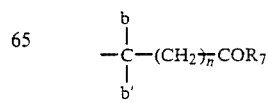

wherein b and b' independently are hydrogen or $C_1$–$C_3$ alkyl, n is 0, 1, 2, or 3; and b and b' when taken together with the carbon to which they are bonded form a 3- to 6-membered carbocyclic ring, and $R_7$ is hydroxy, $C_1$–$C_4$ amino, $C_1$–$C_4$ alkylamino, or di($C_1$–$C_4$ alkyl)amino; or $R_6$ is $C_1$–$C_4$ substituted by phenyl or phenyl substituted by one or two of the same or different groups selected from among $C_1$–$C_4$ alkyl, hydroxy, halogen, carboxy or protected carboxy; or $R_6$ is $C_1$–$C_4$ alkyl substituted by amino or protected amino; or $R_6$ is $C_1$–$C_4$ alkenyl; or $R_6$ is a cyclic lactam group of the formula

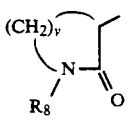

wherein v is 2–4 and $R_8$ is hydrogen or $C_1$–$C_3$ alkyl; or $R_6$ is an aryl methyl group of the formula

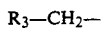

$R_3$—$CH_2$— wherein $R_3$ has the same meanings as defined hereinabove;

The 1-carba(1-dethia)cephems represented by the above formula (1), wherein $R_2$ is hydrogen or a pharmaceutically acceptable salt thereof, inhibit the growth of microorganisms pathogenic to man and animals and may be used to control infectious diseases. The compounds of the invention are obtained in the process provided herein in the same stereochemical form as that of the semi-synthetic cephalosporin antibiotics.

The term "carboxy-protecting group" as used in the specification refers to one of the ester derivatives of a carboxylic acid group commonly employed to block or protect the carboxylic acid group while reactions are carried out on other functional groups on the compound. Examples of such carboxylic acid protecting groups include 4-nitrobenzyl, 4-methylbenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, t-butyl, t-amyl, trityl, 4-methoxytrityl, 4,4'-dimethoxytrityl, 4,4',4''-trimethoxytrityl, 2-phenylprop-2-yl, trimethylsilyl, t-butyldimethylsilyl, phenacyl, 2,2,2-trichloroethyl, β-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl, and like moieties. The species of carboxy-protecting group employed is not critical so long as the derivatized carboxylic acid is stable to the condition of subsequent reaction(s) on other positions of the ring system and can be removed at the appropriate point without disrupting the remainder of the molecule. A preferred carboxylic acid protecting group is the allyl group. Similar carboxy-protecting groups used in the cephalosporin, penicillin and peptide arts can also be used to protect carboxy group substituents of the azetidinone. Further examples of these groups are found in E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5. The related term "protected carboxy" denotes that a carboxy group is substituted with one of the above carboxy-protecting groups.

The term "amino-protecting group" refers to substituents of the amino group commonly employed to block or protect the amino functionality while reacting other functional groups on the compound. Examples of such amino-protecting groups include the formyl group, the trityl group, the phthalimido group, the trichloroacetyl group, the chloroacetyl, bromoacetyl and iodoacetyl groups, urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4 TM bromobenzyloxycarbonyl, 3-bromobenzyloxycarbonyl, 4-nitrobenzyloxycarbonyl, 4-cyanobenzyloxycarbonyl, 2-(4-xenyl)isopropoxycarbonyl, 1,1-diphenyleth-1-yloxycarbonyl,1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2-(methylsulfonyl)ethoxycarbonyl, 2-(triphenylphosphino)ethoxycarbonyl, 9-fluorenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1piperidyloxycarbonyl and the like; the benzoylmethylsulfonyl group, the 2-(nitro)phenylsulfenyl group, the diphenylphosphine oxide group and like amino-protecting groups. Preferred amino-protecting groups are the allyloxycarbonyl, the t-butoxycarbonyl, and the trityl groups. Similar amino-protecting groups used in the cephalosporin, penicillin and peptide art are also embraced by the above terms. Further examples of groups referred to by the above terms are described by J. W. Barton, "Protective Groups In Organic Chemistry", J. G. W. McOmie, Ed., Plenum Press, New York, N.Y., 1973, Chapter 2, and T. W. Greene, "Protective Groups in Organic Synthesis", John Wiley and Sons, New York, N.Y., 1981, Chapter 7. The related term "protected amino" denotes that an amino is substituted with an amino-protecting group discussed above.

In the above definition of the compounds represented by the formula (1), $C_1$–$C_6$ alkyl refers to the straight and branched chain alkyl groups such as methyl, ethyl, n-propyl, isopropyl, n-butyl, t-butyl, n-pentyl, n-hexyl, 3-methylpentyl, and like alkyl groups; $C_1$–$C_6$ alkyl substituted by cyano refers to cyanomethyl, cyanoethyl, 4-cyanobutyl, and the like; $C_1$–$C_6$ alkyl substituted by carboxy refers to such groups as carboxymethyl, 2-carboxyethyl, 2-carboxypropyl, 4-carboxybutyl, 5-carboxypentyl, and the like; $C_1$–$C_6$ alkyl substituted by halogen refers to chloromethyl, bromomethyl, 2-chloroethyl, 1-bromoethyl, 4-chlorobutyl, 4-bromopentyl, 6-chlorohexyl, 4-fluorobutyl, 3-fluoropropyl, fluoromethyl, and the like; $C_1$–$C_6$ alkyl substituted by amino refers to such groups as 2-aminoethyl, aminomethyl, 3-aminopropyl and 4-aminobutyl; $C_1$–$C_6$ alkyl substituted by $C_1$–$C_4$ alkoxy refers to methoxymethyl, 2-methoxyethyl, 2-ethoxyethyl, ethoxymethyl, 3-propoxypropyl, 3-ethoxybutyl, 4-t-butyloxybutyl, 3-methoxypentyl, 6-methoxyhexyl, and like group; $C_1$–$C_6$ alkyl substituted by $C_1$–$C_4$-alkylthio refers to such groups as for example methylthiomethyl, 2-methylthioethyl, 2-ethylthiopropyl, 4-methylthiobutyl, 5-ethylthiohexyl, 3-t-butylthiopropyl, and like groups; $C_1$–$C_6$ alkyl substituted by trifluoromethyl is exemplified by 2,2,2-trifluoroethyl, 3,3,3-trifluoropropyl, 4,4,4-trifluorobutyl, and the like; and $C_1$–$C_6$ alkyl substituted by trifluoromethylthio refers to, for example, trifluoromethylthiomethyl, 2-trifluoromethylthioethyl, 2-trifluoromethylthiopropyl, 4-trifluoromethylthiobutyl, 5-trifluoromethylthiohexyl, and like $C_1$–$C_6$ alkyl substituted groups.

When in the formula (1) R is a substituted phenyl group wherein the substituent(s) are represented by a and a', examples of such groups are halophenyl such as 4-chlorophenyl, 3-bromophenyl, 2-fluorophenyl, 2,4-dichlorophenyl, and 3,5-dichlorophenyl; hydroxyphenyl such as 2-hydroxyphenyl, 3-hydroxyphenyl, 4-hydroxyphenyl, 2,4-dihydroxyphenyl, and 3,4-dihydroxyphenyl; alkoxyphenyl, such as 2,6-dimethoxyphenyl, 4-methoxyphenyl, 3-ethoxyphenyl, 3,4-dimethoxyphenyl, 4-t-butyloxyphenyl, 4-methoxy-3-ethoxyphenyl, and 4-n-propoxyphenyl; alkanoyloxyphenyl such as 2-acetoxyphenyl, 4-propionoxyphenyl, 4-formyloxyphenyl, 4-acetoxyphenyl, 3-butyryloxyphenyl, and 3-acetoxyphenyl; alkylphenyl such as 4-methylphenyl, 2-methylphenyl, 2,4-dimethylphenyl, 3-t-butylphenyl, 4-ethylphenyl, 4-ethyl-3-methylphenyl, and 3,5-dimethylphenyl; alkylthiophenyl such as 4-methylthiophenyl, 3-n-butylthiophenyl, 2-ethylthiophenyl, 3,4-dimethylthiophenyl, and 3-n-propylthiophenyl; aminophenyl such as 2-aminophenyl, 4-aminophenyl, 3,5-diaminophenyl, and 3-aminophenyl; alkanoylamino such as 2-acetylamino, 4-acetylamino, 3-propionylamino, and 4-butyrylamino; alkylsulfonylamino such a 3-methylsulfonylamino, 4-methylsulfonylamino, 3,5-(dimethylsulfonylamino)phenyl, 4-n-butylsulfonylaminophenyl, and 3-ethylsulfonylaminophenyl; carboxyphenyl such as 2-, 3-, or 4-, carboxyphenyl, 3,4-dicarboxyphenyl, and 2,4-dicarboxyphenyl; carbamoylphenyl such as 2-carbamoylphenyl, 2,4-dicarbamoylphenyl, and 4-carbamoylphenyl; hydroxymethylphenyl such as 4-hydroxymethylphenyl and 2-hydroxymethylphenyl; aminomethylphenyl such as 2-aminomethylphenyl and 3-aminomethylphenyl; and carboxyphenyl such as 2-carboxymethylphenyl, 4-carboxymethylphenyl, and 3,4-dicarboxymethylphenyl; and the substituted phenyl groups bearing different substituents such as 4-chloro-3-methylphenyl, 4-fluoro-3-hydroxyphenyl, 3,5-dichloro-4-hydroxyphenyl, 4-hydroxy-3-chlorophenyl, 4-hydroxy-3-methylphenyl, 4-ethyl-3-hydroxyphenyl, 4-methoxy-3-hydroxyphenyl, 4-t-butyloxy-2-hydroxyphenyl, 4-acetylamino-3-methoxyphenyl, 3-amino-4-ethylphenyl, 2-aminomethyl4-chlorophenyl, 2-hydroxymethyl-3-methoxyphenyl, 2-hydroxymethyl-4-fluorophenyl, 2-acetoxy-4-aminophenyl, 4-acetoxy-3-methoxyphenyl, 3-isopropylthio-4-chlorophenyl, 2-methylthio-4-hydroxymethylphenyl, 4-carboxy-3-hydroxyphenyl, 4-ethoxy-3-hydroxyphenyl, 4-methylsulfonylamino-2-carboxyphenyl, 4-amino-3-chlorophenyl, and 2-carboxymethyl-4-hydroxyphenyl.

When R is a substituted phenyl group and a' or a is a $C_1$–$C_4$ haloalkyl or $C_1$–$C_4$ perhaloalkyl, examples of such substituents include chloromethyl, iodomethyl, trichloromethyl, trichloroethyl, 2-bromo-2-methylpropyl, chloropropyl, and fluoromethyl.

Examples of the formula (1) wherein R is a group represented by the formula

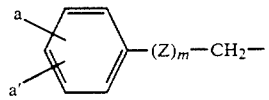

with m=0 are: phenylacetyl, 4-hydroxyphenylacetyl, 4-chlorophenylacetyl, 3,4-dichlorophenylacetyl, 4-methoxyphenylacetyl, 3-ethoxyphenylacetyl, 2-aminomethylphenylacetyl, 3-carboxyphenylacetyl, 4-acetoxyphenylacetyl, 3-aminophenylacetyl, and 4-acetylaminophenylacetyl; and with m=1 and Z=0, phenoxyacetyl, 4-chlorophenoxyacetyl, 4-fluorophenoxyacetyl, 3-aminophenoxyacetyl, 3-hydroxyphenoxyacetyl, 2-methoxyphenoxyacetyl, 2-methylthiophenoxyacetyl, 4-acetylaminophenoxyacetyl, 3,4-dimethylphenoxyacetyl, and 3-hydroxymethylphenoxyacetyl; and with m=1 and Z=S, phenylhioacetyl, 4-chlorophenylthioacetyl, 3,4-dichlorophenylthioacetyl, 2-fluorophenylthioacetyl, 3-hydroxyphenylthioacetyl, and 4-ethoxyphenylthioacetyl.

Examples of compounds of formula (1) when R is $R_3CH_2$- wherein $R_3$ is an aryl group are: naphthyl, 2-thienylacetyl, 3-thienylacetyl, 2-furylacetyl, 2-benzothienylacetyl, 2-benzofurylacetyl, indol-2-ylacetyl, 1H-tetrazol-1-ylacetyl, oxazol-2-ylacetyl, oxazol-4-ylacetyl, thiazol-4-ylacetyl, 2-aminothiazol-4-ylacetyl, 1,3,4-oxadiazol-2-ylacetyl, 1,3,4-thiadiazol-2-ylacetyl, 5-ethyl-1,3,4-thiadiazol-2-ylacetyl and benzoaminothiazoyl, and like aryl groups optionally substituted by amino, $C_1$–$C_4$ alkylsulfonylamino, hydroxy, halo, $C_1$–$C_4$ alkyl or $C_1$–$C_4$-alkoxy groups.

Examples of formula (1) compounds wherein R is a substituted methyl group represented by the formula $R_4$—CH(Q)— and Q is amino, carboxy, hydroxy, or sulfo, are 2-carboxy-2-phenylacetyl, 2-carboxy-2-(4-hydroxyphenyl)acetyl, 2-amino-2-phenylacetyl, 2-amino-2-(4-hydroxyphenyl)acetyl, 2-amino-2-(3-chloro-4-hydroxyphenyl)acetyl, 2-amino-2-(cyclohex-1,4-dien-1-yl)acetyl, 2-hydroxy-2-phenylacetyl, 2-formyloxy-2-phenylacetyl, 2-sulfo-2-phenylacetyl, 2-sulfo-2-(4-methylphenyl)acetyl, and 2-acetoxy-2-(3-hydroxyphenyl)acetyl, 2-amino-2-(2-thienyl)acetyl, 2-amino-2-(3-benzothienyl)acetyl, 2-amino-2-(1H-tetrazol-1-yl)acetyl, 2-hydroxy2-(1,3,4-thiadiazol-2-yl)acetyl, 2-amino-2-(2-aminothiazol-4-yl)acetyl, 2-carboxy-2-(2-thienyl)acetyl, 2-carboxy-2-(benzothien-2-yl)acetyl, and 2-hydroxy-2-(benzofur-2-yl)acetyl; and when Q is a substituted amino group represented by the formula

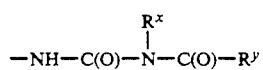

examples of such acyl groups are 2-(N-methyl-N-benzoylcarbamoylamino)-2-phenylacetyl, 2-(N-methyl-N-cinnamoylcarbamoylamino)-2-(2-furyl)acetyl, 2-(N,N-dimethylcarbamoylureido)-2-(4-chlorophenyl)acetyl, 2-[N-methylN-(2-chlorocinnamoyl)carbamoylamino]-2-(2-thienyl)acetyl, and 2-(N-ethyl-N-acetylcarbamoylamino)-2-(4-hydroxyphenyl)acetyl; and when Q is a substituted amino group represented by the formula

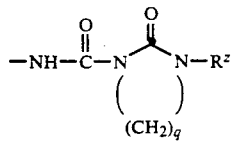

examples are 2-[(3-methylimidazolidin-2-one-1-yl)carbonylamino]-2-phenylacetyl, 2-[(3-acetylimidazolidin-2-one-1-yl)carbonylamino]-2-phenylacetyl, 2-[(3-methylsulfonylimidazolidin-2-one-1-yl)-2-(2-thienyl)acetyl, and 2-[(3-acetylhexahydropyrimidin-2-one-1-yl)carbonylamino-2-phenylacetyl; and when Q is a hydroxy-substituted benzamido group represented by the formula

examples of such acyl groups are 2-(2,4-dihydroxybenzamido)-2-phenylacetyl, 2 TM (4-hydroxybenzamido)-2-(4-hydroxyphenyl)acetyl, 2-(3,4-dihydroxybenzamido)-2-(2-aminothiazol-4-yl)acetyl, 2-(3,5-dihydroxybenzamido)2-(3-thienyl)acetyl, and 2-(2-hydroxybenzamido)-2-(2-benzofuryl)acetyl.

When Q is an hydroxy-substituted pyridinecarbonylamino group, examples include e.g., 2-hydroxypyridin-4-one-6-ylcarbonylamino and 3-hydroxypyridin4-one-6-ylcarbonylamino. When Q is a pyridylcarbonylamino group examples are e.g., pyridin-3-ylcarbonylamino, 4-aminopyridin-3-ylcarbonylamino, 5-chloropyridin-2-ylcarbonylamino, 3-carboxypyridin-4-ylcarbonylamino, and 4-aminopyridino-2-ylcarbonylamino. When Q is an imidazole or pyrazole group as defined above examples include e.g., 2-aminoimidazol-4-ylcarbonylamino, 5-carboxy-2-methylimidazol-4-ylcarbonylamino, 5-carboxypyrazol-3-ylcarbonylamino, 3-aminopyrazol-4-ylcarbonylamino and 4-hydroxypyrazol-5-ylcarbonylamino. When Q is a benzpyridazin-4-one-3-ylcarbonylamino group, examples of Q are represented by the formulae

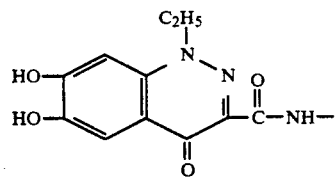

and

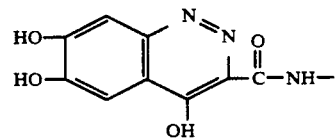

Examples of the compounds represented by formula (1) when R is a keto group or an oximinosubstituted group represented by the formulae

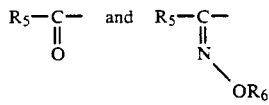

are the keto groups 2-oxo-2-phenylacetyl, 2-oxo-2-(2-thienyl)acetyl, 2-oxo-2-(2-aminothiazol-4-yl)acetyl; and oximino-substituted groups 2-phenyl-2-methoxyiminoacetyl, 2-(2-thienyl)-2-ethoxyiminoacetyl, 2-(2-furyl)-2-methoxyiminoacetyl, 2-(2-benzothienyl)-2-carboxymethoxyiminoacetyl, 2-(2-thienyl)-2-(2-carboxyethoxy)iminoacetyl, 2-(2-amino-1,2,4-thiadiazol-4-yl)-2-methoxyiminoacetyl, 2-(2-aminothiazol-4-yl)-2-methoxyiminoacetyl, 2-(2-chlorothiazol-4-yl)-2-methoxyiminoacetyl, 2-(2-aminothiazol-4-yl)-2-(2-carboxyprop-2-yl)oxyiminoacetyl, 2-(2-aminothiazol-4-yl)-2-(2-carbamoylprop-2-yl)oxyiminoacetyl, 2-(5-amino-1,3,4-thiadiazol-2-yl)-2-methoxyiminoacetyl, 2-(2-aminothiazol-4-yl)-2-(pyrrolidin-2-one-yl)oxyiminoacetyl, 2-(2-aminothiazol-4-yl)-2-(1-methylpyrrolidin-2-one-3-yl)oxyiminoacetyl, 2-phenyl-2-(pyrrolidin-2-one-3-yl)oxyiminoacetyl, 2-(2-aminooxazol-4-yl)-2-(1-ethylpyrrolidin-2-one-3-yl)oxyiminoacetyl, 2-(2-aminothiazol-4-yl)-2-(1-ethylpiperidin-2-one-3-yl)-2-oxyiminoacetyl, and 2-(2-furyl)-2-(pyrrolidin-2-one-3-yl)oxyiminoacetyl.

Examples of the compounds represented by formula (1) when R is a group of the formula

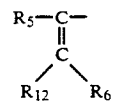

may be found in Hamashima, U.S. Pat. No. 4,634,617, incorporated herein by reference. Exemplary substituents are for $R_{12}$, hydrogen, for $R_5$, phenyl, furyl, thienyl, oxazolyl, isoxazolyl, optionally protected aminoisoxazolyl, thiazolyl, optionally protected aminothiazolyl, thiadiazolyl, and aminothiazolyl, and for $R_6$, $C_1$-$C_3$ alkenyl and —$CH_2CO_2H$.

When $R_6$ of formula (1) is $C_1$-$C_4$ alkyl substituted by phenyl or substituted phenyl, such groups are exemplified by benzyl, 4-hydroxybenzyl, 4-chlorobenzyl, 3-carboxybenzyl, 3-chloro-4-hydroxybenzyl, 2-phenylethyl, 1-phenylethyl, 3-phenylpropyl, 4-hydroxy-2-phenylpropyl, 3-phenylbutyl and like phenylalkyl groups.

When $R_6$ represents $C_1$-$C_4$ alkyl substituted by amino or pro:ected amino, examples include 2-aminoethyl, 3-aminopropyl, 4-aminobutyl, 2-aminopropyl and such groups wherein the amino group is protected by an aminoprotecting group.

When $R_6$ is a $C_2$-$C_4$ alkenyl group, examples include allyl, butene-2, butene-3, butene-1, and like groups.

$R_2'$ may be those 2-position side chains known in the carbacephalosporin art and include hydrogen, $C_1$-$C_5$ alkyl, $C_1$-$C_5$ alkyl substituted with halo, halogen, hydroxy, $C_1$-$C_5$ alkoxy, $C_1$-$C_5$ acyloxy, $C_1$-$C_5$ acyl, $C_1$-$C_5$ alkylthio, and nitrile. These and other such substituents may be found in Hirata et al. 4,302,540, Hirata et al. 4,291,164, Hirata et al. 4,734,494, all incorporated herein by reference.

Examples of the above-defined 1-carbacephalosporins are described below in Table 1 wherein the terms in the column headings refer to formula (1).

TABLE 1

| R | $R_1$ | $R_2$ |
|---|---|---|
| phenyl | H | H |
| 2,6-dimethoxyphenyl | H | H |
| phenylmethyl | H | H |
| 2-aminomethylphenyl-methyl | H | H |
| phenoxymethyl | H | H |
| phenylthiomethyl | H | H |
| 4-chlorophenylthiomethyl | H | H |
| 2-thienylmethyl | $OCH_3$ | H |
| 2-thienylmethyl | H | H |
| 2-furylmethyl | H | H |
| 4-pyridylthiomethyl | H | H |
| α-aminobenzyl | H | H |
| α-carboxybenzyl | H | H |
| αhydroxybenzyl | H | H |
| 2-aminothiazol-4-ylmethyl | H | H |
| (2-aminothiazol-4-yl)methoxyiminomethyl | H | H |
| (1H)tetrazolylmethyl- | H | H |
| (2-aminothiazol-4-yl)(2-carboxyprop-2-yl)oxyiminomethyl- | | |
| α-amino-1,4-cyclodienyl-methyl | H | H |
| 4-aminopyridin-3-ylmethyl | H | H |
| α-sulfoaminobenzyl | H | H |
| α-sulfoaminothien-2-ylmethyl | H | H |
| 4-aminopyridazin-3-ylmethyl | H | H |
| (2-aminothiazol-4-yl)(carboxymethoxyimino)methyl- | H | Na+ |
| (2-aminothiazol-4-yl)(2-carboxyprop-2-yl)oxyiminomethyl- | H | K+ |
| 2-thienylmethyl- | H | Li+ |
| 2-aminothiazol-4-yl(syn-methoxyimino)methyl- | H | H |
| H | H | benzyl |
| $CH_3$— | H | benzyl |
| $NCCH_2$— | H | benzyl |
| Cl—$CH_2$— | H | pMB |
| $CF_3SCH_2$— | H | H |

TABLE 1-continued

| R | $R_1$ | $R_2$ |
|---|---|---|
| 2,6-dimethoxyphenyl | H | Na— |
| 4-methylphenyl | H | pMB |
| 4-chlorophenyl | H | benzyl |
| 3-hydroxyphenyl | H | benzyl |
| phenoxymethyl | H | benzyl |
| phenoxymethyl | H | pNB |
| 4-chlorophenoxymethyl | H | H |
| 4-hydroxyphenoxymethyl | H | H |
| benzyl | H | H |
| benzyl | H | benzyl |
| 4-fluorophenylthiomethyl | H | H |
| 4-chlorobenzyl | H | H |
| 2-aminomethylbenzyl | H | H |
| 3-carboxymethylbenzyl | H | H |
| 2-thienylmethyl | H | benzyl |
| 2-thienylmethyl | H | pNB |
| 2-benzothienylmethyl | H | H |
| 2-benzofurylmethyl | H | H |
| 1,3,4-thiadiazol-2-ylmethyl | H | H |
| 1,3,4-oxadiazol-2-ylmethyl | H | H |
| α-aminobenzyl | H | pMB |
| α-aminobenzyl | H | 2,2,2-trichloroethyl |
| α-amino-(4-hydroxybenzyl) | H | H |
| α-amino-(3-methylsulfonylaminobenzyl) | H | H |
| α-formyloxybenzyl | H | H |
| α-carboxy-(4-hydroxybenzyl) | H | H |
| α-sulfobenzyl | H | H |
| α-[$N^3$-methyl-$N^3$-(2-chlorobenzoyl)ureido]benzyl | H | H |
| α-[$N^3$-(methylaminocarbonyl)$N^3$-methylureido]-4-hydroxybenzyl | H | H |
| α-(3-acetylimidazolidin-2-one-1-yl-carbonylamino)benzyl | H | H |
| α-(3-methylsulfonylimidazolidin-2-one-1-ylcarbonylamino)benzyl | H | H |
| α(4-ethylpiperizin-2-dione-1-yl carbonylamino)benzyl | H | H |
| α-(4-hydroxybenzamido)benzyl | H | H |
| α-(3,4-dihydroxybenzamido)benzyl | H | H |

The 3-trifluoromethyl-carbacephems of formula (1) may be made by routes as set out in the Schemes set forth below.

SCHEME 1

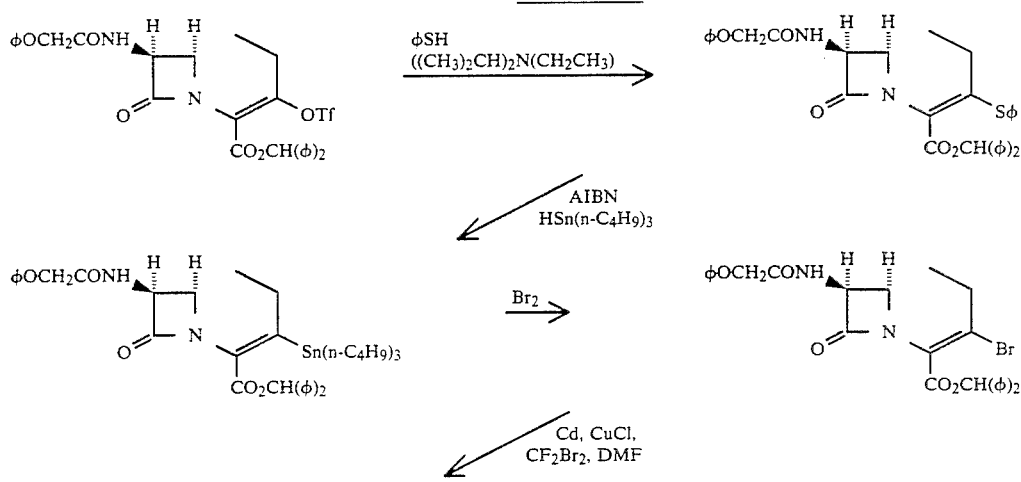

-continued
SCHEME 1

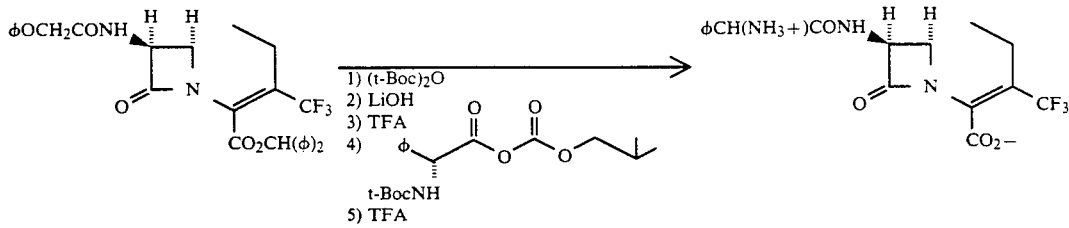

The 3-trifluoromethanesulfonyloxy ("triflate" or "Tf") carbacephem starting material of Scheme 1 may be prepared by the method of Evans et al., U.S. Pat. No. 4,673,737, incorporated herein by reference. This 3-triflate starting material is first reacted with thiophenol under $N_2$ in the presence of an amine, and preferably a tertiary amine such as triethylamine or diisopropylethylamine, to provide benzhydryl 7-β-phenoxyacetylamino-1-carba(1-dethia)-3-phenylthio-3-cephem-4-carboxylate. The 3-phenylthio intermediate is then reacted under $N_2$ with tributyltin hydride in the presence of a free-radical initiator such as 2,2'-azo(bis-)isobuturylnitrile (AIBN) and heated, preferably to about 120° C., to provide the 3-(tri-n-butyl) stannane intermediate as depicted. This tin intermediate is combined with a positive halogenating agent, and preferably bromine, to provide benzhydryl-7β-phenoxyacetylamino-1-carba(1-dethia)-3-bromo-3-cephem-4-carboxylate. The 3-bromo intermediate is then heated (preferably to about 70° C.) and is combined with a mixture of cadmium, cuprous chloride, dibromodifluoromethane and DMF to provide benzhydryl-7β-phenoxyacetylamino-1-carba (1-dethia)3-trifluoromethyl-3-cephem-4-carboxylate. While DMF is preferred, other suitable compounds include those of the group having the formula

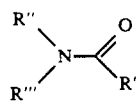

wherein R' is hydrogen or $C_1$-$C_4$ alkyl, R" and R''' are independently $C_1$-$C_4$ alkyl, or together, with the nitrogen, form a saturated ring, such as pyrrolidine or piperidine. This intermediate is then acylated with di-t-butyl dicarbonate ((t-BOC)$_2$O), followed by treatment with a base such as LiOH to provide the 7β-(t-butyloxycarbonylamino) intermediate (not shown). (Further details of this interchange of the t-butoxycarbonyl protecting group for the phenoxyacetyl protecting group can be found in European Patent Application No. 8836996.5, Publication No. 0301877, .)

The t-butoxycarbonyl (t-BOC) group and the benzhydryl ester can then be removed using known methodology, e.g. with trifluoroacetic acid (TFA) in the presence of anisole. The resulting 7-amino-3-trifluoromethyl nucleus intermediate is then N-acylated with an activated form of the desired 7-acyl group. In Scheme (1), the D-phenylglycyl group is introduced by reaction of the 7-amino nucleus intermediate with the t-boc protected anhydride of D-phenylglycine, formed with t-boc protected phenylglycine and isobutyl chloroformate, represented below.

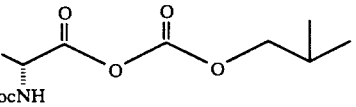

Any remaining t-butoxycarbonyl protecting groups can then be removed by treatment with trifluoroacetic acid. While the phenoxyacetyl and t-butoxycarbonyl (t-Boc) groups were used as amino-protecting groups and the benzhydryl group as a carboxy-protecting group, one of ordinary skill in β-lactam chemistry will appreciate that other carboxy and amino protecting groups will serve as functional equivalents.

The process in Scheme 1 is carried out under substantially anhydrous conditions which represents reaction conditions which are virtually free from water. Accordingly, solvents are dried prior to use in the process. Suitable organic solvents include methylene chloride, chloroform, methyl alcohol, toluene, and dior trichloroethane, tetrahydrofuran (THF), dimethylpropylene urea (DMPU), hexamethylphosphoric triamide (HMPA), dimethyl acetamide, tetrahydropyran, dioxane, acetonitrile, diethyl ether, dimethylacetamide, dimethylsulfoxide, dimethoxyethane, and mixtures thereof.

Free radical initiators are described in an article by Laird and Jorgensen, entitled "Free Radical Chain Reaction", *J. Org. Chem.*, Vol. 55, No. 1, pp. 9–27 (1990), incorporated herein by reference. Suitable free radical initiators include AIBN, Bu$_3$ SnH, Cl$_3$CBr benzoyl peroxide and others listed in the above-referenced article on page 19, under Table VI. Other initiators include photolysis, $X_2$ wherein X=Cl, Br, and I (Schlecker, Henkel, Seebach, Chem. Ber. 110, 2880 (1977)), Oz (Russell, Kaup, J.A.C.S., 91, 3851 (1967)), metal salts (Toong, Yates, *J. Chem. Soc., Chem. Commun.*, 205 (1978)), and esters of thiohydroxamic acids (Barton, Crich, Kretzachman, Tetra. Let., 25, 1955 (1984)).

The term positive halogenating agent is defined as being a compound having an electrophilic halogen, or in other words, the compound provides a halogen having a positive charge. Examples of such include e.g., SbF$_5$, F$_2$, IF$_5$, BrF$_3$, SF$_4$, Cl$_2$, HOCl, (CH$_2$CO)$_2$Cl, N-chlorosuccinamide, Me$_3$COCl, NO$_2$Cl, SO$_2$Cl$_2$, Br$_2$, 1,3-dibromohydantoin, N,N-dibromobenzensulphonamide, HOBr, N-bromosuccinamide, C$_4$H$_8$O$_2$Br$_2$, ICl, IBR, I$_2$, N-iodosuccinamide, and 1,3-diiodo-5,5-dimethylhydantoin.

Scheme (2) below depicts the synthesis of compounds of Formula (1), using the method of Scheme (1), coupled with the use of a p-nitrobenzyl carboxyprotecting group instead of benzhydryl.

SCHEME 2

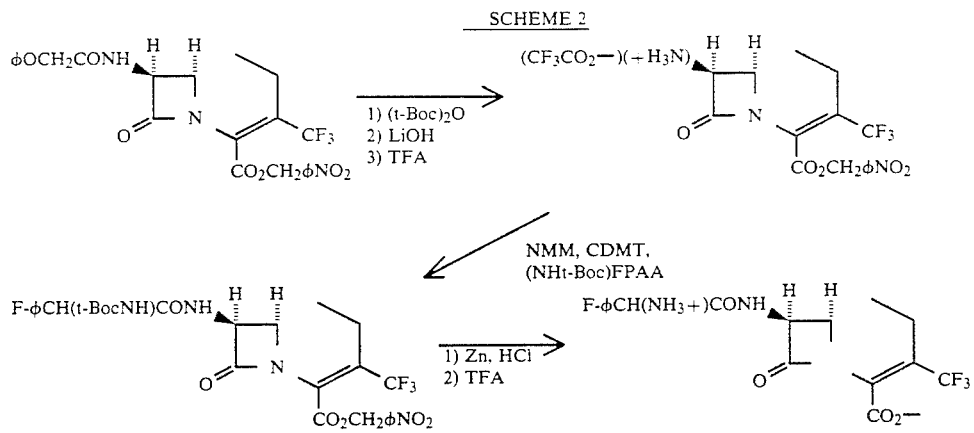

The trifluoro acetate salt intermediate is then treated with a mixture of N-methyl morpholine (NMM), (t-butoxylcarbonylamino)-3-fluorophenylacetic acid (NHt-Boc-FPAA), and 1-chloro-3,5-dimethoxytriazine (CDMT), to prepare the t-Boc protected intermediate. The intermediate is then treated with zinc and HCl, followed by treatment with trifluoroacetic acid.

Alternatively, the 3-trifluoromethyl carbacephems of Formula (1) may be prepared as depicted in Scheme (3).

SCHEME 3

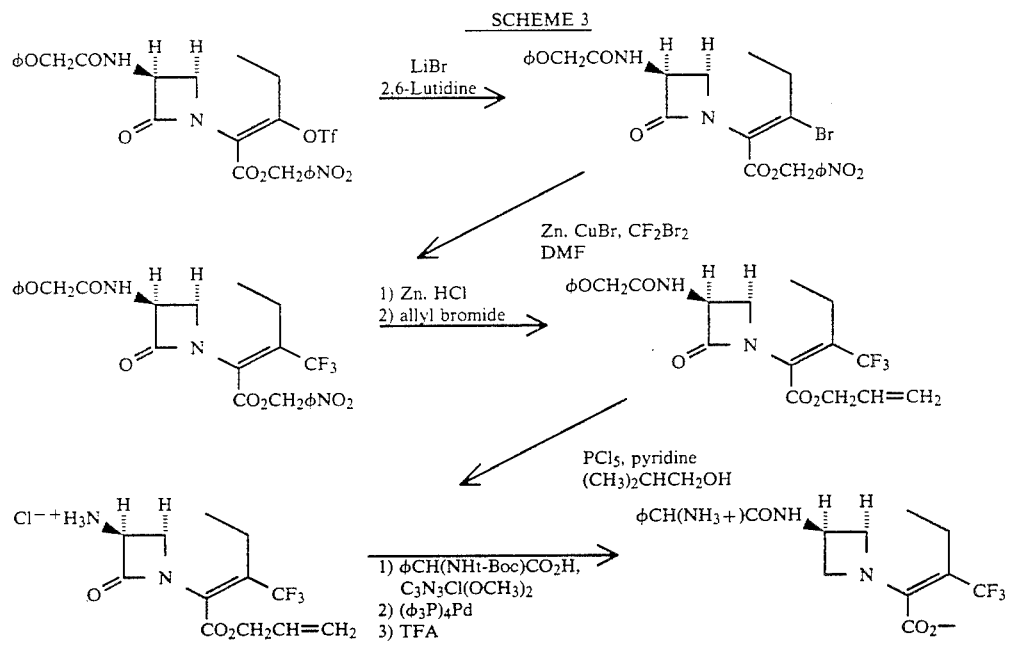

In Scheme (3), the 3-triflate intermediate in an anhydrous organic solvent is converted to the 3-bromo intermediate by a displacement reaction using a bromide containing salt, preferably LiBr, in the presence of a hindered amine base. Bromide containing salts include alkali metal bromide, tetraalkylammoniumbromide, and tetraalkylphosphoniumbromide. A preferred hindered amine base is 2,6-lutidine. This 3-bromo intermediate is then converted directly to the 3-trifluoromethyl intermediate by treatment with a mixture of zinc and dibromodifluoromethane in the presence of cuprous bromide and DMF. The p-nitrobenzyl 7β-phenoxyacetylamino-1-carba(1-dethia)-3-trifluoromethyl-3-cephem-4-carboxylate intermediate is treated with Zn/HCl to remove the p-nitrobenzyl ester group and is then re-esterified with allyl bromide. The phenoxyacetyl group is removed using known methodology, i.e., $PCl_5$/pyridine/isobutyl alcohol, to provide allyl 7η-amino-1-carba(1-dethia)-3-trifluoromethyl-3-cephem-4-carboxylate hydrochlor ide. This intermediate can then be treated with an activated form of the desired carboxylic acid providing the 7-acyl substituent much in the same fashion as is depicted in Scheme (1). The 4-allyl carboxy protecting group may then be removed using known deprotection methodology, i.e., tetrakistriphenylphosphine palladium (O) followed by removal of the t-boc protected group with trifluoroacetic acid to provide compounds of Formula (1). As in Scheme 1, the amino and carboxy protecting groups used are illustrative, with one of ordinary skill in the β-lactam art appreciative that other protecting groups may be employed.

In both Schemes 1 and 3, the 3-bromo intermediate is exposed to a mixture of a cuprous halide (Br,Cl,I), dihalodifluoromethane, either cadmium or zinc, and DMF or a group of the formula

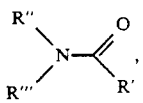

where R', R", and R'" are as defined previously. It is believed that this mixture results in an in-situ generation of trifluoromethyl copper which reacts with the 3-bromo intermediate to form the 3-trifluoromethyl intermediate. Preferably, at least one molar equivalent of trifluoromethyl cadmium or trifluoromethyl zinc is present with the copper, so as to at least theoretically provide at least one molar equivalent of trifluoromethyl copper.

The displacement reaction in which the 3-triflate is converted to the 3-bromo intermediate is more fully set out in Scheme 4.

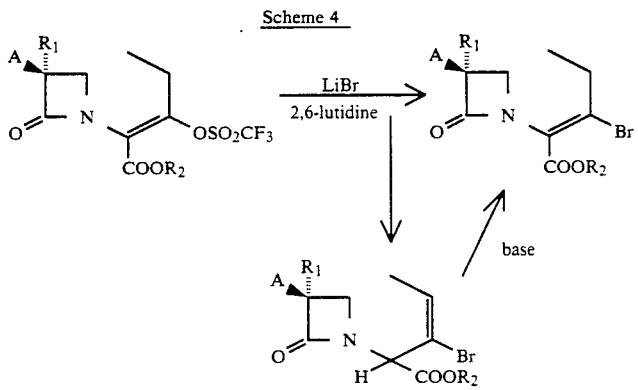

In Scheme 4, $R_1$ and $R_2$ are as defined previously, while A is a protected amino or acylamino of the formula

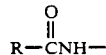

wherein R is as defined previously. The reactions take place in aprotic solvents such as those previously listed. The 3-triflate is combined with lithium bromide and preferably 2,6-lutidine. The mixture is heated to between about 60–70° C., and preferably to about 65° C. and is maintained for a time sufficient to provide the 3-bromo compound. The time for heating is preferably above 16 hours and more preferably is about 48 hours. Normally, the resultant products include a mixture of the Δ2/Δ3 isomers. The Δ2 isomer may then be isomerized to the Δ3 isomer by contacting the Δ2 isomer with a strong base such a 1,8-diazabicyclo[5.4.0]undec-7-ene (DBU) or 1,5-diazabicyclo[4.3.0]non-5-ene (DBN). As disclosed, the 3-bromo compound is a useful intermediate for the production of compounds represented by formula (1). It should be understood, however, that the 3-bromo compounds themselves are useful antibiotics. Therefore, the 3-bromo intermediate may be converted like the 3-trifluoromethyl to form 1-carba(1-dethia)-3-cephem-3-bromo4-carboxylic acids or pharmaceutically acceptable salts thereof. For example, in Scheme 3, the step of converting the 3-bromo to the 3-trifluoromethyl may be omitted to form (3-bromo)cephems.

The term hindered amine base includes both aromatic and aliphatic hindered amines. Aromatic hindered amines would include those with an alkyl substituent bonded to the aromatic carbon adjacent the nitrogen. Preferred substituents would be those larger than methyl such as ethyl, isopropyl, t-butyl, and aryl. More preferred aromatic amines would be those hindered amines with at least both aromatic carbons adjacent the nitrogen substituted with such substituents as $C_1$–$C_6$ alkyls and $C_1$–$C_4$ alkoxys. Further, bicyclic and polycyclic amines can be used as long as at least one carbon adjacent the nitrogen contains an appropriate substituent. Aliphatic hindered amines may also be used and include tertiary amines such as diisopropylethylamine, ethyldiphenylamine, etc.

In one of its aspects, this invention provides 7β-amino-1-carbacephalosporin compounds and salts and esters thereof useful as intermediates in the preparation of the antibiotics represented by formula (1). These intermediates are represented by formula (2):

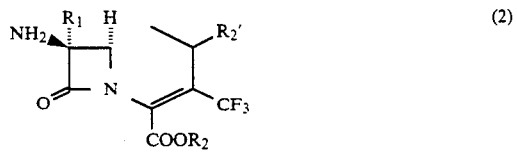

(2)

wherein $R_1$, $R_2$, and $R_2'$ are as defined above for formula (1), the acid addition salts thereof and, when $R_2$ is hydrogen, the alkali metal, alkaline earth metal and amine salts thereof. The 7-amino compounds of formula (2) form salts with common acids such as the mineral acids, e.g., hydrochloric, hydrobromic, sulfuric, and phosphoric; and organosulfonic acids, e.g., methanesulfonic, n-butanesulfonic, benzenesulfonic, p-toluene-sulfonic and naphthalenesulfonic. Such salts are used for isolating and purifying the 7-amino acids and esters thereof. The compound of formula (2) may also form salts with the alkali and alkaline earth metal hydroxides, carbonates, and bicarbonates. Examples of such salts are sodium, potassium, calcium and magnesium salts. Salts may be formed with amines such as dibenzylamine, cyclohexylamine, triethylamine, ethanolamine, diethanolamine, and the like.

The 7β-amino-1-carba-3-cephem compounds of formula (2) are N-acylated with a carboxylic acid RCOOH or a reactive derivative thereof to provide a compound of Formula (1). The N-acylation can be carried out by employing the general acylation methods used for the N-acylation of the cephalosporin nuclei e.g., 7-ACA and 7-ADCA. For example, the nucleus (2) is coupled with the acid RCOOH in the presence of a dehydrating agent such as a carbodiimide e.g., dicyclohexylcarbodiimide. Alternatively the carboxylic acid can be converted to a reactive derivative of the carboxy group and the reactive derivative used in the N-acylation. Reactive derivatives of the carboxy group that can be used are the acid halides, acid azides, and acid anhydrides such as active esters formed with ethyl chloroformate and isobutyl chloroformate; phenylcarbamates; N-hydroxyimides such as formed with N-hydroxysuccinimide and N-hydroxyphthalimide; and those formed with hydroxybenztriazole (HBT); and like active carboxy derivatives. During the N-acylation, any free amino or carboxy groups present in the carboxylic acid RCOOH are desirably protected.

In a further aspect of this invention, there is provided an intermediate of the formula

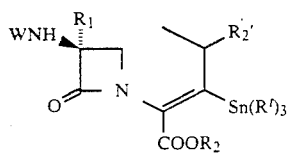

wherein $R_1$, $R_2$, and $R_2'$ are as defined previously, $R'$ is a $C_1$–$C_6$ alkyl or aryl, and W is an amino-protecting group 1 or an acyl group derived from carboxylic acid.

The term aryl is defined to be a monocyclic arene in which there is a conceptual removal of a hydrogen atom from a carbon atom on the ring, such as phenyl, tolyl, and dimethylphenyl, and includes aryls substituted with $C_1$–$C_6$ alkyls.

The term "acyl group derived from a carboxylic acid" includes those 7-position side chains known in the carbacephalosporin and cephalosporin arts and those 6-position side chains known in the penicillin art, and can be represented by

wherein R is as defined above.

In a further aspect of this invention there is provided a preferred embodiment of the invention having the formula

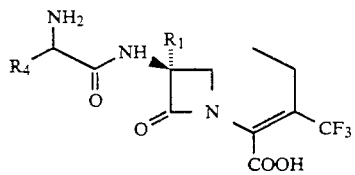

wherein $R_1$ and $R_4$ are as defined previously, and the pharmaceutically acceptable salts thereof. More preferred compounds are represented when $R_4$ is $R_3$ as defined previously and include, e.g., thienyl, furyl, benzofuryl, benzothienyl, benzoaminothiazolyl, phenyl, substituted phenyl, and cyclohexadienyl. Especially preferred compounds are those in which $R_4$ is phenyl, 4-hydroxyphenyl, or 2-aminothiazole compounds.

In another aspect of this invention, there is provided a process for preparing a compound of the formula

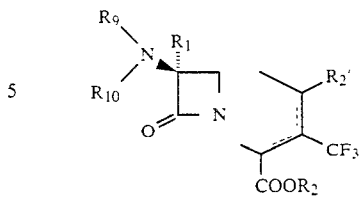

which includes reacting a compound of the formula

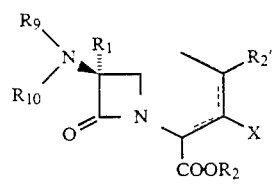

with a mixture of a cuprous halide, cadmium or zinc, dihalodifluoromethane, and either DMF or a group of the formula

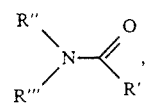

wherein R', R", and R'" are as defined previously; or with trifluoromethyl copper, in a substantially anhydrous inert organic solvent, wherein X is halogen, $R_2$, $R_2'$, and $R_1$ are as defined above and the group $R_9R_{10}N$- is a protected amino group or $R_9$ is hydrogen and $R_{10}$ is an acyl group derived from a carboxylic acid. The process may take place at a temperature range of between about 10° to 90° C., and preferably about 60° C.

A further aspect of this invention provides a process for preparing a compound of the formula

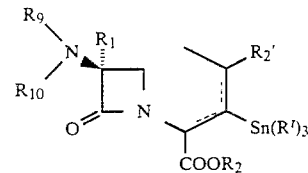

which includes reacting a compound of the formula

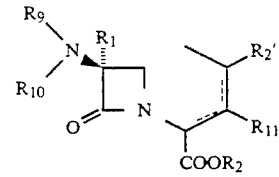

in an inert organic solvent or neat (absent a solvent) with at least one equivalent of a compound having the formula $HSn(R')3$ in the presence of a free radical initiator where $R_1$, $R_2$, $R_2'$, $R_9$, $R_{10}$, and $R'$ are as defined above and $R_{11}$ is the residue of a $C_1$–$C_{10}$ hydrocarbylthiol or $C_1$–$C_{10}$ hydrocarbylselenyl. The reaction preferably is heated to a temperature of about 120° C.

The terms "residue of a $C_1$–$C_{10}$ hydrocarbylthiol" and "residue of a $C_1$–$C_{10}$ hydrocarbylselenyl" are defined to be the groups R/S- and R/Se-, respectively, wherein $R^j$ is $C_1$-$C_{10}$ alkyl; $C_1$-$C_{10}$ alkyl substituted by hydroxy, $C_1$-$C_4$ alkoxy, $C_1$-$C_4$ alkylthio, trifluoromethyl, carboxy, carbamoyl, amino, $C_1$-$C_4$ alkylamino, di-($C_1$-$C_4$ alkyl)amino, halogen, cyano, phenyl, or substituted phenyl as defined above for R; $C_2$-$C_{10}$ alkenyl; $C_3$-$C_7$ cycloalkyl; phenyl or substituted phenyl as defined above for R; or a 5- or 6-membered heterocycle selected from thienyl, furyl, pyrrolyl, imidazolyl, pyrazolyl, oxazolyl, isoxazolyl, thiazolyl, benzoaminothiazolyl, isothiazolyl, oxadiazolyl, thiadiazolyl, triazolyl, tetrazolyl, pyridyl, pyrimidyl, triazinyl, or pyrazinyl; the benzheterocycles, benzothienyl, benzofuryl, indolyl, benzimidazolyl, or benztriazolyl, and said 5- or b 6-membered heterocycle and said benzheterocycle substituted by $C_1$-$C_4$ alkyl, halogen, hydroxy, $C_1$-$C_4$ alkoxy, amino, carboxy, cyano, or carbamoyl; and when said heterocycle or benzheterocycle contains a basic ring nitrogen, the $C_1$-$C_4$ alkyl quaternary salt thereof.

A further aspect of this invention provides a process of preparing a compound of the formula

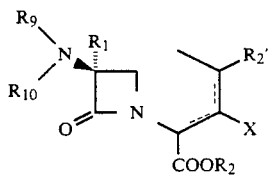

which includes reacting a compound of the formula

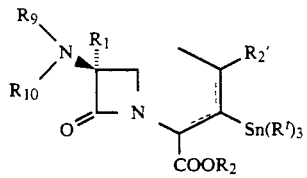

in an inert organic solvent with a positive halogenating agent, preferably in the amount of about 1.0 to 1.2 equivalents, wherein $R_1$, $R_2$, $R_2'$, $R_9$, $R_{10}$, and $R^t$ are as defined above, and X is fluoro, chloro, bromo, or iodo. The temperature range for the reaction is between about $-78°$ C. to room temperature (21° C.), and preferably is about between $-78°$ to $-40°$ C.

This invention also provides a process for the preparation of a compound of formula (3)

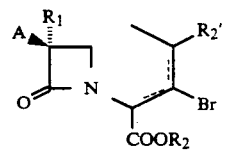 (3)

wherein $R_1$ $R_2$, and $R_2'$ are as defined previously and A is an amino, a protected amino or a group of the formula

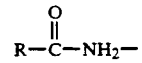

wherein R is as defined previously, by reacting a compound of the formula

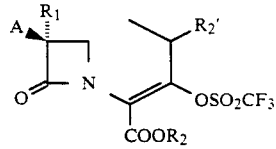

in the presence of a bromide containing salt such as an alkali metal bromide, tetraalkylammoniumbromide, and tetraalkylphosphoniumbromide, and preferably LiBr, and a hindered amine base, such as 2,6-lutidine, for a time and at a temperature sufficient to prepare compound (3). Further, the preferred temperature range is between about 21° C.-70° C., with about 65° C. being most preferred. Also, the invention encompasses the above process including an isomerization step in which the Δ2 isomer is converted to the Δ3 isomer by exposing the Δ2 isomer to a strong base such as DBU or DBN.

Further, the invention encompasses compounds of formula (3), per se. It should be understood that when A is $NH_2$, the compound of formula (3) will form salts as discussed with respect to formula (2), and may be acylated likewise.

This invention also provides a method for treating infectious diseases in man and other animals and pharmaceutical formulations suitable for administration in the treatment method. The therapeutic method of this invention comprises administering to a man or animal an antibiotically effective non-toxic dose of a compound represented by formula (1) and, for that matter, formula (3), wherein $R_2$ is hydrogen or a pharmaceutically acceptable salt thereof.

The 1-carbacephalosporins provided by the invention form salts with suitable bases, in particular, the pharmaceutically acceptable, non-toxic salts. The carboxy group of the 1-carbacephalosporin can form salts with the alkali and alkaline earth metal hydroxides, carbonates and bicarbonates. Examples of such pharmaceutically acceptable salts are the sodium, potassium, calcium, and magnesium salts. Salts also may be formed with amines such as dibenzylamine, dicyclohexylamine, triethylamine, ethanolamine, di-ethanolamine, and like amines. Likewise, when the 1-carbacephalosporin is substituted by two or more carboxy groups, di- and trisalts are obtained by conventional salt-forming methods.

1-Carbacephalosporin compounds presented by the invention with an amino group substituent in the 7-position side chain forms salts with suitable acids to provide the antibiotics as pharmaceutically acceptable salts. Examples of suitable acids are hydrochloric, hydrobromic, sulfuric, and phosphoric.

1-Carbacephalosporins presented by the invention with when $R_2$ is hydrogen may form the zwitterionic (inner-salt) form of the compound when the 7-position substituent includes a free amino.

An antibiotically effective amount is an amount between about 25 mg and about 2 grams. The compound, salt or ester, may be administered in a single dose or in multiple doses throughout the day. Treatment may continue for a week to ten days or longer depending upon the duration of the infection. The particular dose and regimen can depend on such factors as the weight and age of the patient, the particular causative organism, the severity of the infection, the general health of the patient, and the tolerance of the individual to the antibiotic.

The 1-carba(1-dethia)cephem may be administered parenterally, orally, subcutaneously or rectally. As with other β-lactam antibiotics the method of this invention may be used prophylactically to prevent infections after exposure or before possible exposure e.g., preoperatively. The antibiotic 1-carba(1-dethia)cephem may be administered by conventional methods e.g., in capsules, tablets, suppositories, by syringe, or by intravenous drip.

The pharmaceutical formulations of the invention comprise an antibiotically effective non-toxic amount of a 1-carba(1-dethia)3-cephem represented by the formula (1) or formula (3) wherein $R_2$ is hydrogen or a pharmaceutically acceptable salt thereof, and a pharmaceutical carrier.

The pharmaceutically acceptable salts are useful forms of the antibiotics for preparing antibiotic formulations. Formulations for oral administration include capsules, tablets, lozenges, and liquid suspensions. The antibiotic or a salt or ester thereof in the form of a dry powder is encapsulated in gelatin capsules for oral use. The antibiotic may also be blended with an excipient e.g., a stabilizer prior to filling. Capsules may contain between about 100 mg and about 500 mg to provide unit dosage formulations.

Tablets containing between about 100 mg and 500 mg of the antibiotic or a salt or ester thereof are formulated by conventional means and may contain in addition a binding agent, disintegrating agent, stabilizing agent, antioxidant, etc.

Liquid preparations of the antibiotic may be prepared for infant and geriatric use. Pediatric suspensions are formulated with the antibiotic oral excipients such as suspending agents, flavoring agents, stabilizers and the like. Solutions of the antibiotics likewise may be formulated with solubilizing agents, flavoring agents, sugar, water, etc.

Parenteral formulations of the antibiotics for injection are formulated with Water-for-Injection, Ringer's solution, physiological saline, or glucose solution. The antibiotic also may be administered in an intravenous fluid by the drip method.

For parenteral use the antibiotic, or its derivative, is made up preferably in dry crystalline powder form or as a lyophilized powder and filled into vials. Such vials contain between about 100 mg and about 2 grams of antibiotic per vial.

The following abbreviations have the indicated meanings: t-boc = t-butoxycarbonyl or t-butyloxycarbonyl; HPLC = high performance liquid chromatography; THF = tetrahydrofuran, J = coupling constant for NMR spectra in Hz; DMF = N,N-Dimethylformamide; DMPU = Dimethyl propylene urea; BSU = bis(trimethyl silyl)urea; BSA = bis(trimethyl silyl)acetimide; DMAP = Dimethylaminopyridine; DBU = 1,8-Diazabicyclo[5.4.0]-undec-7-ene; AIBN = Azo(bis)isobuturylnitrile; DCC = Dicyclohexylcarbodiimide; TFA = Trifluoroacetic acid; HMPA = Hexamethylphosphoric triamide; DMSO = Dimethylsulfoxide.

EXPERIMENTAL SECTION

PREPARATION 1

Diphenylmethyl[7S,6R]-7-phenoxyacetamido-3-phenylthio-1-carba(1-dethia)-3-cephem-4-carb oxylate A solution of diphenylmethyl[7S,6R]-7-phenoxyacetamido-3-trifluoromethylsulfonyloxy-1-carba(1-dethia)-3-cephem-4-carboxylate (40.0 g, 63.00 mmol) in 180 ml anhydrous acetonitrile was treated under $N_2$ with diisopropylethylamine (15.4 ml, 88.0 mmol) and thiophenol (7.1 ml, 69.0 mmol). The reaction was stirred overnight at ambient temperature. The solvent was removed in vacuo and the residue was purified by chromatography on silica gel (elution with 35:65 ethyl acetate/hexane) giving 33.45 g (90%) of a light yellow solid.

$^1$H NMR (CDCl$_3$):δ 7.2–7.6 (m, 19H), 7.08 (t, J=7Hz, 1H), 7.05 (s, 1H), 6.90 (d, J=8Hz, 2H), 5.44 (m, 1H), 4.54 (s, 2H), 3.81 (dt, J=5, 12Hz, 1H), 2.0–2.3 (m, 2H), 1.7–1.8 (m, 1H), and 1.3–1.5 (m, 1H).

PREPARATION 2

Diphenylmethyl[7S,6R]-7-phenoxyacetamido-3-bromo-1-carba(1-dethia)-3-cephem-4-carboxyla te Diphenylmethyl[7S,6R]-7-phenoxyacetamido-3-trifluoromethylsulfonyloxy-1-carba(1-dethia)-3-ceph em-4-carboxylate (150 g, 0.238 moles) was dissolved in 1600 ml anhydrous DMF and treated with 2,6-lutidine (63.8 g, 0.595 moles) and lithium bromide (121.1 g, 1.43 moles). The reaction was heated to 65° C over 30 minutes and maintained at this temperature for 64 hours. The reaction was cooled to ambient temperature and 75% of the solvent was removed under reduced pressure at 50° C. The slurry was diluted with ethyl acetate/ether, washed with NaHCO$_3$ (3×), 1N HCl (3×), and brine, dried over MgSO$_4$, filtered through silica gel with 10% ethyl acetate/CH$_2$Cl$_2$, and evaporated at reduced pressure until a solid started to precipitate out. A beige solid (34.4 g) was collected and upon further evaporation of the mother liquors, an additional 10.6 g solid could be collected. These two batches of solids were combined as both were the desired Δ3 isomers (the titled product). The remaining liquid was stripped to dryness leaving 64.7 g of a mixture of Δ2/Δ3 isomers. The mixture of olefin isomers were equilibrated as follows. Dissolution of the mixture (64.7 g, 0.115 moles) in 675 ml anhydrous CH$_2$Cl$_2$ was followed by treatment with DBU (4.7 g, 0.031 moles). After three hours at ambient temperature, the reaction was filtered through silica gel with 10% ethyl acetate/CH$_2$Cl$_2$ and evaporated. The residue was dissolved in a small amount of ethyl acetate, diluted with hexane and cooled to 0° C. This produced 17.6 g clean Δ3 isomer and the remaining 39.4 g (from the mother liquor) was chromatographed on silica gel (eluted with a gradient of toluene to 30/70 ethyl acetate in toluene). This produced 31.5 g of a Δ2/Δ3 mixture, which was dissolved in ethyl acetate, diluted with hexane, seeded with the product and chilled to 0° C. This gave 18.2 g of the Δ-3 isomer leaving 14.2 g Δ2/Δ3 mixture. A total of 80.8 g of the titled product was isolated in a yield of 61%.

PREPARATION 3

Allyl[7S,6R]-7-phenoxyacetylamino-3-bromo-1-carba(1-dethia)-3-cephem-4-carboxylate (a) Allyl[7S,6R-7-phenoxyacetylamino-3-trifluoromethylsulfonyloxy-1-carba(1-dethia)-3-cephem-4-carboxylate (1.0 g, 1.9826 mmoles) and dried lithium bromide (0.689 g, 7.9302 mmoles) were combined with DMF (3.0 ml). The mixture, after all solids were dissolved, was slowly heated to approximately 67° C. and stirred for 16 hours. The mixture was cooled to room temperature and was combined with 75 ml EtOAc, 50 ml 1:1 H$_2$O/saturated NaHCO$_3$ solution. The organic materials were separated and washed with 50 ml 1N HCl, dried with Na$_2$SO$_4$, filtered and concentrated to a reddish brown oil. Flash chromatography eluting with 7% EtOAc/CH$_2$Cl$_2$ yielded 87 mg of the product or approximately a 10% yield.

(b) The 3-triflate of (a) above (200 mg, 0.3965 mmoles) was combined with dried lithium bromide (138 mg, 1.586 mmoles) and DMPU (2 ml) and the mixture heated to 65°-67° C. for six hours. To the mixture, 2,6-lutidine (0.4362 mmoles) was added and the mixture stirred at 67° C. overnight (14 hours). The mixture was poured into 50 ml EtOAc and 20 ml saturated NaHCO$_3$ solution. The organics were washed with 25 ml of 1N HCl, and separated, dried with Na$_2$SO$_4$, filtered and concentrated to a brownish-yellow oil. Flash chromatography eluting with 7% EtOAc/CH$_2$Cl$_2$ provided 45 mg (26%) of a 60/40 mixture of Δ2 to Δ3 isomers.

(c) The procedure was followed as outlined in (b) except that the 2,6-lutidine was placed in the mixture at the start of the procedure instead of after heating begun. The amounts used were:
3-triflate starting material: 200 mg, 0.3965 mmoles
2,6-lutidine: 0.793 mmoles, 92 μl
Lithium bromide: 138 mg, 1.586 mmol
DMPU: 2 ml
This preparation resulted in 55 mg (31.2%) of a 60/40 Δ2/Δ3 ratio.

(d) The procedure was followed as outlined in (c) except DMF replaced DMPU. The amounts used were:
3-triflate starting material: 145 mg, 0.2875 mmoles
2,6-lutidine: 0.5749 mmoles, 67 μl
Lithium bromide: 100 mg, 1.15 mmoles
DMF: 1.5 ml
This preparation resulted in 61.2 mg (49%) of a 70/30 mixture of Δ2/Δ3 isomers.

(e) The procedure was followed as outlined in (d), except that the mixture was heated for approximately 2½ times longer, or 48 hours. The amounts used were:
3-triflate starting material: 11 gr, 21.808 mmoles
2,6-lutidine: 43.616 mmoles, 5.08 ml
Lithium bromide: 7.6 g, 87.232 mmoles
DMF: 120 ml
This preparation resulted in 4.6 g of the titled product, or 48.5% yield of a mixture of Δ2/Δ3 isomers at a >95/5 ratio, respectively. Data for the Δ2 isomer:

$^1$H NMR (300 MHz, CDCl$_3$) δ7.32 (t, J=Hz, 2H), 7.10 (d, J=9 Hz, 1H), 7.05 (t, J=6Hz, 1H), 6.92 (d, J=8 Hz, 2H), 6.50 (m, 1H), 5.95 (m, 1H), 5.35 (m, 3H), 4.90 (s, 1H), 4.68 (m, 2H), 4.55 (S, 2H), 4.15 (m, 1H), 2.35 (m, 1H), and 2.15 (m, 1H).

IR (CHCl$_3$) 3019, 1771, 1747, 1691, 1517, 1495, 1236, and 1182 cm$^{-1}$

MS, m/e 434 (M$^+$), 436 (M$^+$+2) Analysis for C$_{19}$H$_{17}$N$_2$O$_5$Br Calculated: C, 52.43; H, 4.40; N, 6.44; Found: C, 52.23; H, 4.36; N, 6.37.

EXAMPLE 1

Diphenylmethyl[7S,6R-7-phenoxyacetamido-3-tributylstannyl-1-carba(1-dethia)-3-cephem-4-ca rboxylate A suspension of diphenylmethyl[7S,6R]-7-phenoxyacetamido-3-phenylthio-1-carba(1-dethia)-3-ceph em-4-carboxylate (37.0 g, 62.7 mmol) in 32 ml anhydrous diglyme was treated under N$_2$ with tributyltin hydride (42.1 ml, 157.0 mmol) and azo(bis)isobutyryl nitrile (AIBN) (12.4 ml, 75.2 mmol). The reaction was heated to 120° C. for 45 min and then cooled to ambient temperature. The residue was purified by chromatography on silica gel (elution with 40:60 ethyl acetate/hexane). This produced 37.1 g of a clear viscous oil (77%).

$^1$H NMR (CDCl$_3$):δ7.55 (d, J=7 Hz, 2 H), 7.44 (d, J=7Hz, 2H), 7.2–7.4 (m, 7H), 7.0–7.1 (m, 2H), 6.9 (m, 3H), 5.48 (m, 1H), 4.56 (s, 2H), 3.87 (m, 1H), 2.6–2.7 (m, 1H), 2.3–2.45 (m, 1H), 1.9–2.0 (m, 1H), 1.2–1.4 (m, 12H), and 0.8–0.85 (m, 15H); IR(CHCl$_3$: 2958.2, 2923.7, 1766.2, 1689.9, 1523.0, 1496.2, 1374.4, and 1239.5 cm$^{-1}$; MS(FAB):m/e (M+) 771; UV (EtOH):λmax 275 nm (ε9960); Analysis: C$_{41}$H$_{52}$N$_2$O$_5$Sn; C,H,N.

EXAMPLE 2

Diphenylmethyl[7S,6R]-7-phenoxyacetamido-3-bromo-1-carba(1-dethia)-3-cephem-4-carboxyla te The stannane from Example 1 (8.58 g, 11.13 mmoles) in 400 ml anhydrous THF was cooled in a dry-ice/acetone bath and treated dropwise with a solution of Br$_2$ (1.78 gr., 11.13 mmoles) in 100 ml THF over 30 min. The solvent was removed at reduced pressure and chromatographed on silica with 40:60 ethyl acetate/hexane producing 5.02 g (80%) of a white solid.

$^1$H NMR (CDCl$_3$):δ7.2–7.5 (m, 12H), 7.0–7.1 (m, 2H), 6.98 (s, 1H), 6.9 (d, J=8Hz, 2H), 5.40 (m, 1H), 4.54 (s, 2H), 3.95 (m, 1H), 2.7–2.8 (m, 2H), 1.9–2.0 (m, 1H), 1.5–1.7 (m, 1H), and 1.3–1.4 (m, 1H); IR (CHCl$_3$: 3025.2, 1787.0, 1742.2, 1692.7, 1600.6, 1518.9, 1496.0, 302.3, and 1242.7 cm$^{-1}$; MS(FAB): m/e (M$^+$ 561; UV (EtOH): λmax 275 nm (ε4870); Analysis: C$_{29}$H$_{25}$BrN$_2$O$_5$; C,H,N.

EXAMPLE 3

Diphenylmethyl[7S,6R]-7-phenoxyacetamido-3-trifluoromethyl-1-carba(1-dethia)-3-cephem-4-carboxylate A suspension of cadmium (20.0 g, 178 mmoles) in 100 ml anhydrous DMF was cooled in an ice-bath under N$_2$ and treated dropwise with CF$_2$Br$_2$. Periodic removal of the ice-bath was necessary to keep the reaction proceeding smoothly. After addition was complete the bath was removed and the reaction was stirred at ambient temperature for 1 h. In a separate flask the starting 3-bromo intermediate (10.0 g, 17.8 mmoles) was dissolved in 18 ml anhydrous DMPU and heated to 70° C. The solution of cadmium reagent was treated with CuCl (17.6 g, 178 mmoles) and the resulting reddish-brown solution was added to the 3-bromo intermediate via cannula over 1 hour. After cooling to ambient temperature the mixture was diluted with ethyl acetate, filtered through celite, washed with water and brine, dried over MgSO$_4$ and reduced to a brown oil in vacuo. This oil was chromatographed on silica gel with 40:60 ethyl acetate/hexane giving 4.7 g (49%) of the titled product as a foam.

$^1$H NMR (CDCl$_3$):δ7.3–7.4 (m. 12H), 7.0–7.2 (m, 3H), 6.9 (d, J=8Hz, 2H), 5.49 (m, 1H), 4.58 (s, 2H), 3.96 (m, 1H), 2.3–2.5 (m, 2H), 2.0–2.1 (m, 1H), and 1.4–1.5 (m, 1H); IR (CHCl$_3$): 1787.0, 1742.2, 1692.7, 1600.6, 1518.9, 1496.0, 1302.3, and 1242.7 cm$^{31}$ $^1$; MS(FAB):m/e (M$^+$ + 1) 517; UV (EtOH): λmax 264 nm (ε 8946);
Analysis: C$_{30}$H$_{25}$F$_3$N$_2$O$_5$; C,H,N.

EXAMPLE 4

Diphenylmethyl7S,6R]-7-t-butoxycarboxamido-3-trifluoromethyl-1-carba(1-dethia)-3-cephem-4-carboxylate Diphenylmethyl[7S,6R]-7-phenoxyacetamido-3-trifluoromethyl-1-carba(1-dethia)-3-cephem-4-carboxylate (4.7 g, 8.5 mmoles) was dissolved in 85 ml anhydrous CH$_2$Cl$_2$ under N$_2$, cooled in an ice-bath and treated with di-t-butyldicarbonate (2.04 g, 9.35 mmoles) and dimethylamino pyridine (DMAP) (0.52 g, 4.3 mmoles). After 45 minutes, the reaction was warmed to ambient temperature for 4 hours. The solution was filtered through silica with 20:80 ethyl acetate:CH$_2$Cl$_2$. After the solvent was removed in vacuo, the residue was taken up in 85 ml anhydrous THF and chilled in an ice-bath. LiOH (9.7 ml of a 1M solution) was added dropwise and the solution was allowed to warm to ambient temperature. The reaction was extracted with ethyl acetate and this extract was washed with 1 N HCl, saturated NaHCO$_2$, brine, dried over anhydous MgSO$_4$ and evaporated in vacuo to dryness. This left 4.2 g crude orange foam.

$^1$H NMR (CDCl$_3$): δ 7.3–7.4 (m, 10H), 6.95 (s, 1H), 5.98 (br d, J=11Hz, 1H), 5.22 (m, 1H), 3.87 (m, 1H), 2.3–2.5 (m, 2H), 2.0–2.1 (m, 1H), and 1.6–1.7 (m, 1H), 1.23 (s, 9H); IR (CHCl$_3$): 1785.3, 1740.0, 1718.5, 1497.3, 1301.7, and 1243.3 cm$^{-1}$; MS (FAB): m/e (M$^+$ + 1) 517; UV (EtOH): λmax 264 nm (ε 8946);

Analysis: C$_{27}$H$_{27}$F$_3$N$_2$O$_5$; C,H,N.

EXAMPLE 5

[7S,6R]-7-Amino-3-trifluoromethyl-1-carba(1-dethia)-3-cephem-4-carboxylic acid, trifluo roacetate salt The product from Example 4 (2.00 g, 3.87 mmoles) was dissolved in cold trifluoroacetic acid (TFA) (40 ml) and triethylsilane (13 ml) under N$_2$ at 0° C. The reaction was maintained at 0° C. for 30 minutes in an ice bath and the ice bath removed and the mixture was stirred for 20 minutes. Anhydrous CH$_3$CN and toluene were added and the volume was reduced in vacuo. This process was repeated and the flask was stripped to dryness. The residue was then suspended in CH$_3$CN and filtered. The solids were washed with CH$_3$CN/diethyl ether and then twice with diethyl ether producing 925 mg (66%) of the titled product as a white solid.

$^1$H NMR (DMSO-d$_6$/TFA):δ 8.0–8.2 (br s, 1H), 4.92 (d, J=6Hz, 1H), 3.97 (m, 1H), 2.0–2.1 (m, 2H), and 1.7–1.8 (m, 2H).

EXAMPLE 6

[7S,6R]-7-[D-alpha-(t-Butoxycarbonylamino)-phenylacetylamino]-3-trifluoromethyl-1-carba(1-dethia)3-cephem-4-carboxylic acid The trifluoroacetate salt from Example 5 (0.90 g, 2.47 mmoles) was suspended in 25 ml ethyl acetate under N$_2$ and was treated with monosilyltrifluoroacetamide (1.51 ml, 8.15 mmoles) and then heated at 35° C. until all solids were in solution. In a separate flask t-BOC phenylglycine was dissolved in 25 ml ethyl acetate under N$_2$, cooled to −45° C. and treated sequentially with isobutyl chloroformate (0.32 ml, 2.47 mmoles) and N-methylmorpholine (0.326 ml, 2.96 mmoles). After 30 minutes, the solution of the amine was cooled to 0° C. and then added via cannula over 5 minutes and stirred for 30 minutes as the temperature rose from −45° C. to −35° C. and for 1.5 hours as the temperature rose to 0° C. At this time 2.0 ml methanol was added, the ice bath was removed and the solution was stirred for 10 minutes as it warmed to ambient temperature. Filtration, evaporation and chromatography on silica with 3% acetic acid in ethyl acetate produced the titled product as a semi-pure beige foam (1.03 g, 87%).

$^1$H NMR (CDCl$_3$):δ 7.1–7.4 (m, 5H), 6.1 (br s, 1H), 5.4 br s, 1H), 3.8 (br m, 1H), 2.2–2.4 (br m, 2H), and 1.2–1.5 (br m, 11H).

EXAMPLE 7

7β-[D-α-(amino)phenylacetylamino]-3-trifluoromethyl-1-carba-(1-dethia)-3-cephem-4-carboxylic acid The t-BOC protected acid from Example 6 was placed in a flask at 0° C. and treated with a mixture of cold trifluoroacetic acid (TFA) (20 ml) and triethylsilane (7 ml). After stirring for 15 minutes at 0° C., the ice bath was removed and the reaction was stirred for a further 10 minutes at ambient temperature, diluted with CH$_3$CN and reduced in volume. Further dilution with CH$_3$CN was followed by evaporation to dryness, suspension of the residue in Et$_2$O and filtration. The resulting solid was washed repeatedly with Et$_2$O and dried in vacuo to 0.74 g crude product of about 85% purity. Reverse phase chromatography on C-18 with a step gradient from 10% CH$_3$CN/H$_2$O to 30% CH$_3$CN/H$_2$O gave 0.39 g (50%) of the titled product as white solid.

$^1$H NMR (D$_1$O):δ 7.5–7.6 (m, 5H), 5.44 (d, J=7 Hz, 1H), 5.21 (s, 1H), 3.95 (m, 1H), 2.25 (br m, 2H), 1.7–1.8 (m, 1H), and 1.0–1.1 (m, 1H); IR (CHCl$_3$): 1776.7, 1740.0, 1693.7, 1561.6, 1300.2, and 1166.1 cm$^{-1}$; MS (FAB) m/e (M$^+$ + 1) 384; UV (EtOH): λmax 257 nm (ε 9190).

EXAMPLE 8

[7S,6R]-7-{[2-(t-Butoxycarbonyl)amino-4-thiazolyl]-(methoxyimino)acetylamido-3-trifluoromethyl 1-carba(1-dethia)-3-cephem-4-carboxylic acid

[7S,6R]-7-Amino-3-trifluoromethyl-1-carba-(1-dethia)-3-cephem-4-carboxylic acid, trifluoroacetate salt (0.10 g, 0.275 mmoles) was treated under N$_2$ with bis(trimethylsilyl)urea (0.281 g, 1.38 mmoles) and 1.4 ml. anhydrous DMF. The solids dissolved after the slurry was warmed to 45° C and the solution was kept at this temperature for 1 hour. In a separate flask, [2-(t-butoxycarbonyl)amino-4-thiazolyl](methoxyimino) acetic acid (0.083 g, 0.275 mmoles) was dissolved in 1.4 ml DMF, cooled to −5° C., treated with oxalyl chloride (0.035 g, 0.275 mmoles), and warmed to ambient temperature over 30 min. The solution of nucleus was cooled to ambient temperature, treated with pyridine (0.067 ml, 0.825 mmoles) and then with the solution of acid chloride. After stirring for 2 hours, the solution was cooled in an ice-bath and treated with 2 ml H$_2$O, diluted with ethyl acetate and partitioned. The organic layer was washed twice with 1N HCL, with H$_2$O, and with brine, dried over MgSO$_4$, filtered, and evaporated to dryness. The crude solid (0.101 g) was flash chromatographed on silica with 4% HOAc in ethyl acetate giving 0.087 g (59%) of the titled product.

EXAMPLE 9

[7S,6R]-7-([2-Amino-4-thiazolyl(methoxyimino)acetyl]amido)-3-trifluoromethyl-1-carba(1-dethia)-3-cephem-4-carboxylic acid A mixture of trifluoroacetic acid (1.5 ml) and triethylsilane (0.5 ml) were cooled in an ice/EtOH bath under N$_2$ and treated with the diphenylmethyl [7S,6R]-7-{[2-(t-butoxycarbonyl)amino-4-thiazolyl](methoxyimino) acetyl}amido-3-trifluoromethyl-1-carba(1-dethia)-3-cephem-4-carboxylate. After 30 minutes, the reaction was treated with CH₃CN and evaporated to dryness. This crude residue (0.055 g) was chromatographed by prep HPLC on a reverse phase column with a 15:84:1 to 20:79:1 step gradient of CH$_3$CN:H$_2$O:HOAc giving 0.021 g of final product.

$^1$H NMR (DMSO-d$_6$):δ 9.25 (d, J=11Hz, 1H), 7.18 (br s, 2H), 6.70 (s, 1H), 5.48 (m, 1H), 3.9 (m, 1H), 3.80 (s, 3H), 2.37 (br m, 2H), 1.95 (m, 1H), and 1.6 (m, 1H).

EXAMPLE 10

[7S,6R]-7-[D-α-(t-Butoxycarbonylamino)-4-hydroxyphenylacetylamino]-3-trifluoromethyl-1-carba(1-dethia)-3-cephem-4-carboxylic acid A solution of [D-α-(t-butoxycarbonylamino)-4-hydroxyphenylacetic acid (0.214 g, 0.799 mM) in 2.4 ml anhydrous THF was treated with 1-hydroxybenzotriazole (0.108 g, 0.799 mM) and DCC (0.198 g, 0.959 mM) at 0° C. A precipitate formed after 5 minutes and the suspension was warmed to ambient temperature and stirred for 2 hours at which time the solution was filtered and cooled to 0° C. The carbacephem zwitterion was suspended in 2.4 ml anhydrous THF and treated with bistrimethylsilylacetimide (BSA) (0.8 ml) giving a solution which was concentrated to a thick oil, diluted with 0.8 ml THF, cooled to 0° C. and treated with the cold solution of active ester. After 30 minutes at 0° C., the bath was removed and the reaction was stirred overnight. The solvent was evaporated and the residue was partitioned between ethyl acetate and aqueous NaHCO₃. The organic was extracted once more with aqueous NaHCO₃ and the combined aqueous layers were layered with ethyl acetate and the pH was lowered to 2.5 with 1N HCl. The aqueous layer was washed with ethyl acetate and the combined organic layers were dried (MgSO₄), filtered and concentrated to provide 0.271 g (67%) of the titled product, which was not further purified.

EXAMPLE 11

[6R,7S]-7β-[D-α-(amino)-4-hydroxyphenylacetylamino]-3-trifluoromethyl-1-carba-1-dethia-3-cephem-4-carboxylic acid The product from Example 10 was placed in a flask at 0° C. and treated with a mixture of cold trifluoroacetic acid (TFA) (2.2 ml) and triethylsilane (0.5 ml). The flask was placed immediately on a rotary evaporator and concentrated to an oil which was triturated with diethyl ether producing a solid, which was collected by filtration and washed with Et₂O. This solid was dried in vacuo for 3 h giving 0.132 g crude product. Reverse phase chromatography on C$_{18}$ with a gradient from 99/1::H$_2$O/HOAc to 5/94/1::CH$_3$CN/H$_2$O/acetic acid gave after lyophilization 0.055 g (25%) of the titled product as a white solid.

$^1$H NMR (D$_2$O):δ 7.35 (m, 2H), 6.97 (m, 2H), 5.40 (d, J=7Hz, 1H), 5.13 (s, 1H), 3.90 (m, 1H), 2.1–2.3 (br m, 2H), 1.73 (m, 1H), and 1.10 (m, 1H); IR (KBr): 1768.0, 1688.9, 1613.6, 1519.1, and 1300.2 cm$^{-1}$; MS (FAB): m/e (M⁺ + 1) 400; UV (ethanol): λmax 234, 257 nm (ε 12800, 9030);

Analysis:
Calc.: C, 51.13; H, 4.04; N, 10.52;
Found: C, 51.25; H, 4.21; N, 10.29.

EXAMPLE 12

[6R,7S]-7-β-[D-α-(amino)-4-fluorophenylacetylamino]-3-trifluoromethyl-1-carba-1-dethia-3-cephem-4-carboxylic acid A solution of racemic t-BOC protected 4-fluorophenylglycine (0.216 g, 0.80 mM) in 8.0 ml ethyl acetate was cooled to −45° C., treated with isobutyl chloroformate (0.104 ml, 0.80 mM) and N-methylmorpholine (0.097 ml, 0.88 mM), and stirred for 30 minutes. The 7-amino-3-trifluoromethyl-1-carba(1-dethia)-3-cephem-4-carboxylic acid (0.200 g, 0.80 mM) was dissolved in 8.0 ml ethyl acetate after the addition of monosilyltrifluoroacetamide (0.341 ml, 1.84 mM) and added to the mixed anhydride at −45° C. After 30 min, the solution was warmed to 0° C. for 1 hour and then treated with 0.5 ml MeOH, warmed to ambient temperature, filtered through celite, and concentrated at 30° C. The product was chromatographed on silica gel with 3/87/10::HOAc/ethyl acetate/hexane. Both diastereomers were seen in the $^1$H-NMR along with minor impurities. The crude product (0.228 g) was treated with cold TFA (1.8 ml) and Et$_3$SiH (0.6 ml), concentrated, triturated with Et$_2$O, collected by filtration, and washed with Et$_2$O. The crude TFA salt (0.209 g) was chromatographed on a C$_{18}$ column with a two step gradient from 15% CH$_3$CN/H$_2$O to 20% CH$_3$CN/H$_2$O giving cleanly after lyophilization both 0.030 g (10%) product from the L-amino acid and 0.046 g (14%) product resulting from the D-amino acid. HPLC retention times: C$_{18}$, 1/20/79: :HOAc/CH$_3$CN/H$_2$O, 2 ml/min, L=4.11 min D=5.38 min. L-diastereomer:

$^1$H NMR (CDCl$_3$):δ 9.1 (m, 1H), 7.50 (m, 2H), 7.22 (t, J =10Hz, 2H), 5.17 (br s, 1H), 4.89 (br s, 1H), 3.76 (m, 1H), 2.17 (m, 2H), 1.73 (m, 1H), 1.60 (m, 1H); IR (CHCl$_3$): cm$^{-1}$; MS (FAB): m/e (M⁺); UV (EtOH): λmax 257 nm (ε).

EXAMPLE 13

[7S,6R]-7-{[2-(Triphenylmethyl)amino-4-thiazolyl](triphenylmethoxyimino)acetyl}amido-3-trifluoromethyl-1-carba(1-dethia)-3-cephem-4-carboxylic acid 7-amino-3-trifluoromethyl-1-carba(1-dethia)3-cephem-4-carboxylic acid (0.300 g, 1.20 mM) (the carbaceph zwitterion) was dissolved in 6.0 ml dry DMF with bistrimethylsilyl urea (BSU) (1.23 g, 6.0 mM) at 50° C. for 1 h and then at ambient temperature for 30 min. In a separate flask, [2-tritylamino-4-thiazolyl(trityloxyimino)acetic acid (0.806 g, 1.20 mM) was dissolved in 6.0 ml dry DMF and cooled to 0° C., treated dropwise with oxalyl chloride (0.105 ml, 1.20 mM), and warmed to ambient temperature. The nucleus was then cooled to 0° C., treated with pyridine (0.194 ml, 2.4 mM) and the acid chloride, warmed to ambient temperature and stirred for 2 h. After dilution with 2.0 ml H$_2$O, the reaction was treated with 1 N HCl and extracted with ethyl acetate. The ethyl acetate layer was washed with H$_2$O, 1 N HCl, H$_2$O, brine, dried over MgSO₄ and concentrated. The crude product (1.12 g) was chromatographed by filtration through silica gel with 3% HOAc/ethyl acetate giving 0.95 g (88%) of the title product as white powder.

EXAMPLE 14

7S,6R]-7-([2-amino-4-thiazolyl(oximino)acetyl]amido)-3-trifluoromethyl-1-carba(1-deth ia)-3-cephem-4-carboxylic acid A solution of the bis-tritylated carbacephem from Example 13 in 4.5 ml THF was treated with 7.6 ml 75% aqueous formic acid and slowly warmed to 40° C. under $N_2$ for 2 h. After cooling, 20 ml, $CH_3CN$ was added followed by concentration and this process was repeated leaving a brown residue. This solid was washed with 3/1::$Et_2O/CH_3CN$ and the solid isolated by centrifugation. After additional washes with $Et_2O$, the solid was chromatographed on HP-20ss with 1% $HOAc/H_2O$ after loading with $CH_3CN$. The resulting solid was chromatographed on $C_{18}$ with 1/10/89::$HOAc/CH_3CN/H_2O$ giving 0.027 g cream colored solid.

$^1$H NMR (DMSO-d$_6$):δ 9.13 (d, J=9Hz, 1H), 7.07 (s, 2H), 6.64 (s, 1H), 5.50 (m, 1H), 3.89 (m, 1H), 2.25 (m, 2H), 1.95 (m, 1H), 1.60 (m, 1H); IR (CHCl$_3$: cm$^{-1}$; MS (FAB): m/e (M+); UV (EtOH): λmax 257 nm.

EXAMPLE 15

Diphenylmethyl[7S,6R]-7-phenoxyacetamido-3-trifluoromethyl-1-carba(1-dethia)-3-cephem-4-carboxylate A suspension of acid-washed zinc (58.2 g, 0.89 moles) in 1780 ml anhydrous DMF under $N_2$ was treated dropwise with 205.4 g (0.98 mmoles) of $CF_2Br_2$. The $CF_2Br_2$ was added so as to maintain a temperature of 45°-50° C. After the addition was complete, the reaction was stirred at ambient temperature for 1.5 hours during which time the mixture returned to room temperature. The solution of the zinc reagent was cooled to −30° C. and treated with DMPU (100 ml) and CuCl (88.1 g, 0.89 mmoles). After 15 minutes, the reaction warmed to 0° C. for 30 minutes. In a separate flask, the diphenylmethyl(6R, 7S)-7-phenoxyacetamido-3-bromo-1-carba(1-dethia)-3-cephem-4-carboxylate (50.0 g, 0.089 moles) was dissolved in anhydrous 100 ml DMPU and 100 ml DMF under $N_2$ and heated to 65° C. The copper solution was added to the bromide via cannula over 1 hour maintaining the temperature at 65° C. After an additional hour, the reaction was cooled to 50° C. and stirred for 16 hours. The reaction was cooled to ambient temperature, diluted with ethyl acetate, poured into saturated NaHCO$_3$, filtered through celite, washed 2× with NaHCO$_3$ (2×), water, 1 N HCl (2×), water and brine, dried over MgSO$_4$ and reduced to a brown oil in vacuo. This oil was filtered through silica gel with 60:40 ethyl acetate/hexane and recrystallized from ethyl acetate/hexane giving 28.4 g (58%) of an off-white solid.

EXAMPLE 16

Allyl[7R,6S]-7-phenoxyacetamido-3-trifluoromethyl-1-carba(1-dethia)-3-cephem-4-carboxyl ate After dissolving the product from Example 15 (26.00 g,0.050 moles) in 375 ml N,N-dimethylformide and 750 ml tetrahydrofuran under $N_2$, 375 ml of 1 N HCl was added followed by zinc dust (19.61 g, 0.30 moles). The solution became warm and it was allowed to stir for 90 minutes and then filtered through celite. The THF was then evaporated. Dilution with ethyl acetate was followed by four washings with 1 N HCl, water, brine, dried over sodium sulfate, and evaporated under reduced pressure to a crude orange solid. The solid was dissolved in ethyl acetate, a 50% aqueous solution of sodium bicarbonate added, and the two-phase solution was treated with tetrabutylammonium hydrogen sulfate (17.83 g, 0.052 moles). After stirring for 15 minutes, the layers were separated, and the ethyl acetate layer dried over sodium sulfate, filtered and evaporated under reduced pressure to a viscous oil. The oil was dissolved in 110 ml chloroform and treated with allyl bromide (7.26 g, 0.060 moles) dissolved in 35 ml chloroform via addition funnel over 30 minutes. The solution was stirred at ambient temperature overnight, reduced to a solid, and chromatographed on silica gel with 70% hexane/30% ethyl acetate to obtain after evaporation under reduced pressure 14.35 g of the titled product (68%).

$^1$NMR (CDCl$_3$):δ 7.45 (d, J=8, 1H), 7.30 (t, J=7, 2H), 7.00 (t, J=7, 1H), 6.87 (d, J=10, 2H), 6.0–5.8 (m, J=1H), 5.45 (dd, J=9, 1H), 5.4–5.2 (m, 2H), 5.72 (t, J=6, 2H), 5.43 (s, 2H), 3.95–3.85 (m, 1H), 2.55–2.4 (m, 1H), 2.4–2.25 (m, 1H), 2.1–1.95 (m, 1H), 1.6–1.4 (m, 1H).

EXAMPLE 17

Diphenylmethyl[7S, 6R]-7-phenoxyacetamido-3-trifluoromethyl-1-carba(1-dethia)-3-cephem-4-carboxylate A suspension of freshly acid-washed zinc dust (58.2 g, 0.89 moles) was suspended in 1780 ml of anhydrous DMF in a three liter three-neck flask equipped with septum, thermometer, $N_2$ line, addition funnel, and dry ice condenser. Approximately 20% of the ice cold dibromodifluoromethane (205.4 g, .98 moles) was added drop-wise at a fast pace via addition funnel, and after 15 minutes initiation of an exothermic reaction caused an increase in temperature to 50° C. The rest of the dibromodifluoromethane was added at a pace that kept the internal temperature of the reaction at 45° –50° C. and then stirred for 90 minutes after addition was complete. After cooling the solution to −30° C., 150 ml of DMPU followed by CuCl (88.1 g,0.89 moles) was added, stirred for 20 minutes, then the bath was replaced with an ice bath and stirred for 20 minutes. In a separate flask the starting vinyl bromide (50.0 g, 0.089 moles) was dissolved in 100 ml anhydrous DMPU and 100 ml anhydrous DMF and heated to 65° –70° C. The cold copper reagent was added to the bromide via canula over approximately one hour, maintaining the temperature at 65° –70° C. during addition and then stirred one hour at 70° C. After cooling to ambient temperature the mixture was diluted with ethyl acetate, poured slowly into 50% aqueous bicarbonate solution, separated, washed two more times with 50% aqueous bicarbonate, water, two times 1N HCl, water, brine, dried over magnesium sulfate, and reduced to a brown oil. The oil was chromatographed on silica gel using 60:40 hexane/ethyl acetate and then crystallized from ethyl acetate/hexane to give 28.4 g beige solid (58%).

EXAMPLE 18 p-Nitrobenzyl[7S, 6R]-7-phenoxyacetamido-3-trifluoromethyl-1-carba (1-dethia)-3-cephem-4 -carboxylate The titled compound was made in a similar fashion to Example 17 (except CuBr was used instead of CuCl) to give 64% yield of a beige solid.

$^1$H NMR (CDCl$_3$):δ 8.19 (d, J=9, 2H), 7.63 (d, J=9, 2H), 7.30 (tr, J=6, 3H), 7.03 (tr, J=8, 1H), 6.86 (d, J=9, 2H), 5.45 (tr, J=5, 1H), 5.37 (quartet, J=15, 2H), 4.45

(s, 2H), 4.0–3.9 (m, 1H), 2.6–2.35 (m, 1H), 2.4–2.3 (m, 1H), 2.1–2.0 (m, 1H), 2.6–2.4 (m, 1H).

EXAMPLE 19

Allyl [7S, 6R]-7-amino-3-trifluoromethyl-1-carba(1-dethia)-3-cephem-4-carboxylate, hydrochloride salt The product from Example 16 (10.53 g, 0.0248 moles) was dissolved in 83 ml dry methylene chloride under $N_2$ and was cooled to 0° C. The solution was treated with pyridine (2.41 g, .0305 moles) via syringe and $PCl_5$ (5.84 g, 0.0280 moles) was then added portionwise over 20 minutes. The ice bath was removed after 30 minutes and the solution was stirred for 1½hours at which time the solution was re-cooled to ice bath temperature and treated with isobutyl alcohol (18.4 g, 0.248 moles) dissolved in 20 ml diethyl ether via syringe over five minutes. After 30 minutes the ice bath was removed and the reaction was stirred one hour. A thick, white, fluffy solid had formed which was cooled to 0° C., collected by filtration, washed two times with a 50/50 mixture of methylene chloride/diethyl ether and one time with diethyl ether. This solid was dried in vacuo for three hours giving 6.49 g of the titled product as a floculent white solid (77%).

$^1$H NMR (DMSO-$d_6$):δ 9.20 (s, 3H), 6.0–5.8 (m, 1H), 5.35 (d J=Hz, 1H), 5.24 (d, J=Hz, 1H), 4.90 (d, J=Hz, 1H), 4.75 (t, 2H), 4.1–3.9 (m, 1H), 3.5–3.2 (m, 2H), 2.2–2.1 (m, 1H), and 1.9–1.7 (m, 1H).

EXAMPLE 20

Allyl 7S 6R]-7-D-α-(t-butoxycarbonylamino)3-fluorophenylacetylamino]-3-trifluoromethyl-1-carba(1-dethia)-3-cephem-4-carboxylate A solution of (t-butoxycarbonylamino)-3-fluorophenylacetic acid (1.05 g,0.00321 moles) in 21 ml anhydrous methylene chloride was treated with N-methylmorpholine (0.035 g,0.00343 moles) and 1-chloro-3,5-dimethoxytriazine (0.58 g,0.00321 moles) at 0° C. under $N_2$ and stirred for 45 minutes. The product from Example 16 (1.00 g, 0.00306 moles) was suspended in 8 ml methylene chloride, treated with N-methylmorpholine (0.35 g, 0.00343 moles), and the resulting solution was added dropwise over ten minutes to the above activated ester solution. After 20 minutes at 0° C., the bath was removed and the solution was stirred 90 minutes. After the solvent was evaporated in vacuo, the residue was dissolved in ethyl acetate, the insolubles removed by filtration through celite, and evaporated to an oil. The crude product was chromatographed on silica gel with 75:25 hexane/ethyl acetate, then 65:45 hexane/ethyl acetate giving 1.45 g (88%) of the titled product as a beige foam.

$^1$H NMR (CDCl$_3$):δ 7.4–7.3 (m, 2H), 7.2–7.0 (m, 2H), 6.75 (d, 1H), 6.0–5.85 (m, 1H), 5.7–5.5 (m, 1H), 5.4–5.2 (m, 2H), 5.2–5.1 (m, 1H), 4.8–4.7 (m, 1H), 3.95–3.8 (m, 1H), 2.6–2.2 (m, 2H), 2.0–1.7 (m, 1H), 1.40 (s, 9H), and 1.3–1.1 (m, 1H).

EXAMPLE 21

[7S,6R]-7-D,L-α-(t-Butoxycarbonylamino)-3-fluorophenylacetylamino)-3-trifluoromethyl-1-carba(1-dethia)-3-cephem-4-carboxylic acid The product from Example 20 (1.45 g, 0.00268 moles) was dissolved in 4.5 ml ethyl acetate and 1 ml methylene chloride under $N_2$ and deoxygenated by bubbling nitrogen into the flask for five minutes. The solution was cooled in an ice bath and treated with 0.070 g tetrakistriphenylphosphine palladium, 0.070 g triphenylphosphine, and 6.4 ml (0.00322 moles) of a 0.5 M solution of sodium 2-ethyl hexanoate in ethyl acetate. After five minutes the ice bath was removed and the solution was stirred 30 minutes at which time the solution was poured into 30 ml of a 50/50 mixture of diethyl ether/hexane. The resulting precipitate was collected by suction filtration, dissolved in ethyl acetate and a small amount of methylene chloride, washed with 1N HCl, dried over magnesium sulfate, and evaporated to provide 1.20 g (89%) of the titled compound, which was not further purified.

EXAMPLE 22

[6R,7S]-7-β-[D-α-(amino)-3-fluorophenylacetylamino]-3-trifluoromethyl-1-carba-1-det hia-3-cephem-4-carboxylic acid The product from Example 21 (1.15 g, 0.00229 moles) was added in one portion to an ice-cooled solution of TFA (11.5 ml) and anisole (0.75 ml, 0.00687 moles) under $N_2$ and stirred 30 minutes. The reaction was diluted with acetonitrile and reduced in volume, and diluted again with acetonitrile followed by evaporation at 30° C. to dryness. The residue was triturated with diethyl ether and the resulting solid was collected by filtration and washed repeatedly with diethyl ether. The crude solid was dried in vacuo to give 0.89 g of a mixture of diastereomers. 0.20 g of product was chromatographed by reverse phase chromatography on C-18 in 0.020 g portions with 10% acetonitrile/1% AcOH/H$_2$O to give after lyophilization 0.032 g product.

EXAMPLE 23

Allyl[7S,6R]-7-α-(t-butoxycarbonylamino)-3-ethylsulfonamidophenylacetylamino]-3-trifluoromethyl-1 -carba(1-dethia)-3-cephem-4-carboxylate The titled compound, prepared in a similar manner to Example 20, yielded a white foam (88%).

$^1$NMR (CDCl$_3$):δ 7.50 (s, 1H), 7.35–7.1 (m, 6H), 6.0–5.75 (m, 2H), 5.4–5.1 (m, 4H), 5.8–5.7 (m, 2H), 3.95–3.8 (m, 1H), 3.10 (q, J=8, 2H), 2.6–2.0 (m, 3H), 1.40 (s, 9H), 1.30 (m, 4H).

EXAMPLE 24

[7S,6R]-7-[D,L-α-(t-Butoxycarbonylamino)-3-ethylsulfonamidophenylacetylamino]-3-trifluoromethyl-1-carba(1-dethia)-3-cephem-4-carboxylic acid The crude titled product was prepared from the product of Example 23 according to the procedure for Example 21 (96%) and was not further purified.

EXAMPLE 25

6R,7S]-7-β-[D-α-(amino)-3-ethylsulfonamidophenylacetylamino]-3-trifluoromethyl-1-carba-1 dethia-3-cephem-4-carboxylic acid The titled product was prepared from the crude product of Example 24 according to the procedure for Example 22 and was chromatographed on a C18 column using 20% acetonitrile/1% ammonium acetate/H$_2$O to give 14% product after lyophilization.

$^1$NMR: (DMSO-$d_6$) δ 9.85 (br s, 1H), 9.3–9.1 (m, 1H), 7.3–7.0 (m, 4H), 5.3–5.2 (m, 1H), 4.72 (s, 1H), 3.7–3.6 (m, 1H), 3.1–2.9 (m, 1H), 2.2–1.9 (m, 2H), 1.4–1.3 (m, 1H), 1.25–0.95 (m, 4H).

EXAMPLE 26

Allyl[7S,6R]-7-[α-(t-butoxycarbonylamino)-3-bromo-phenylacetylamino]-3-trifluoromethyl-1-carba-(1-dethia)-3-cephem-4-carboxylate The titled compound was prepared according to the procedure given for Example 20 and was chromatographed on silica gel using 70/30 hexane/ethyl acetate to yield an off-white foam (91%).

$^1$H NMR (CDCl$_3$): δ 7.5–7.2 (m, 5H), 6.0–5.7 (m, 2H), 5.5–5.2 (m, 3H), 5.0–4.7 (m, 1H), 3.95–3.8 (m, 1H), 2.6–2.2 (m, 2H), 2.1–1.7 (m, 1H), 1.4 (s, 9H), 1.1–1.3 (m, 1H).

EXAMPLE 27

[7S,6R]-7-[D,L-α-(t-Butoxycarbonylamino)-3-bromo-phenylacetylamino]-3-trifluoromethyl-1-carba(1-dethia)-3-cephem-4-carboxylic acid A crude yield of >100% of the titled product was isolated from a similar reaction to Example 21. Starting material was the product from Example 26.

EXAMPLE 28

[6R,7S]-7-β-D-α-(amino)-3-bromophenylacetylamino]-3-trifluoromethyl-1-carba-1-dethia-3-cephem-4-carboxylic acid The titled compound was prepared according to the procedure for Example 26 and was chromatographed using 15% acetonitrile/1%AcOH/H$_2$O to give 10% product.

$^1$NMR (DMSO-d$_6$): δ 9.20 (br s, 1H), 7.65 (s, 1H), 7.50 (d, J=5, 1 Hz, 1H), 7.40 (d, J=5 Hz, 1H), 7.30 (t, J=5 Hz, 1H), 5.3–5.2 (m, 1H), 4.75 (s, 1H), 3.7–3.6 (m, 1H), 2.2–2.0 (m, 2H), 1.4–1.2 (m, 2H).

EXAMPLE 29

Allyl[7S,6R]-7-[α-t-butoxycarbonylamino)-3-tri-fluoromethylphenylacetylamino]-3-trifluoromethyl-1-carba(1-dethia)-3-cephem-4-carboxylate The titled product, prepared in a similar fashion to Example 20 was a white foam (91%).

$^1$NMR (CDCl$_3$): δ 7.4–7.2 (m, 4H), 6.9–6.8 (m, 1H), 6.0–5.85 (m, 1H), 5.7–5.55 (m, 1H), 5.4–5.2 (m, 4H), 4.75 (tr, J=3), 4.0–3.8 (m, 1H), 2.5–2.2 (m, 2H), 2.1–1.7 (m, 1H), 1.7–1.5 (m, 1H), 1.40 (s, 1H).

EXAMPLE 30

[7S, 6R]-7-[D,L-α-(t-Butoxycarbonylamino)-3-trifluorome-thylphenylacetylamino]-3-trifluoromethyl-1-carba(1-dethia)-3-cephem-4-carboxylic acid The titled product was prepared in a similar fashion to Example 21 yielding >100% crude light yellow solid. The starting material was the product from Example 29.

EXAMPLE 31

[6R,7S]-7-β-[D-α-(amino)-3-trifluoromethyl-phenylacetylamino]-3-trifluoromethyl-1-carba-1-carba-1-dethia3-cephem-4-carboxylic acid The titled product was prepared in a similar manner to Example 22, using the product from Example 30 for starting material, and was chromatographed on a C18 column in0.020 g portions using 15% acetonitrile/1% AcOH/H$_2$O to give 12% yield of product.

$^1$NMR (DMSO-d$_6$): δ 9.5–9.3 (m, 1H), 8.6 (br s, 3H), 7.9–7.6 (m, 4H), 5.45–5.35 (m, 1H), 5.16 (s, 1H), 3.85–3.75 (m, 1H), 2.3–2.1 (m, 2H), 1.35–1.25 (m, 1H), 1.25–1.1 (m, 1H).

EXAMPLE 32

[6R,7S]-7-β-[D-α-(amino)-3,4-dichloro-phenylacetylamino-3-trifluoromethyl-1-carba-1-d ethia-3-cephem4-carboxylic acid A racemic solution of t-boc protected 3,4-dichloro-phenylglycine 0.550 g, 0.00173 moles) in 21 ml N,N-dimethylformamide was cooled to −45° C. under N$_2$, isobutyl chloroformate (0.22 ml, 0.00173 moles) followed by N-methylmorpholine (0.19 ml, 0.00173 moles) was added and the solution was stirred for 30 minutes. Monosilyltrifluoroacetamide (1.53 ml, 0.00824 moles) was added to a stirred suspension of 7-amino-3-tri-fluoromethyl-1-carba(1-dethia)-3-dephem-4-carboxylic acid (0.600 g, 0.00165 moles) in 15 ml N,N-dimethylformamide and the solution was heated to 40° C for 30 minutes. The solution of silylated nucleus was cooled and added to the mixed anhydride at a rate that kept the internal temperature of the reaction at −40° C. The solution was slowly warmed to 0° C. after two hours, 1.2 ml MeOH added, and the ice bath removed. After reaching ambient temperature the solution was diluted with ethyl acetate, filtered through celite, washed four times with 1N HCl, H$_2$O, brine, dried over magnesium sulfate, and concentrated under reduced pressure. The residue was chromatographed on silica gel with 2/80/18:HOAc/ethyl acetate/hexane. The crude product was added to a stirred solution of TFA (4.0 ml) and Et$_3$SiH (1.2 ml) in an ice bath, and after 30 minutes the solution was concentrated, triturated with diethyl ether, collected by filtration, and washed with diethyl ether. Chromatography of the crude TFA salt (0.114 g) on a C18 column using a gradient to 25% CH$_3$CN/H$_2$O gave after lyophilization 0.021 g (3%) of a mixture of diastereomers (90% D-side chain and 10% L-side chain by HPLC).

$^1$NMR (DMSO-d$_6$): δ 9.15 (br s, 1H), 7.7–7.6 (m, 2H), 7.38 (d, J=8 Hz, 1H), 5.3–5.25 (m, 1H), 4.75 (s, 1H), 3.8–3.7 (m, 1H), 2.2–2.1 (m, 2H), 1.4–1.2 (m, 2H).

EXAMPLE 33

[6R,7S]-7β-D-α-(amino)-3-chloro-4-hydroxy-phenylacetylamino-3-trifluoromethyl-1-carba-1-dethia-3-cephem-4-carboxylic acid The titled product was prepared by the same reaction conditions as Example 32, except pure t-boc protected D-3-chloro-4 hydroxyphenyl glycine was used for the acylation to give 41% yield as a white solid.

$^1$NMR (DMSO-d$_6$): δ 7.40 (s, 1H), 7.15 (d, J=9 Hz, 1H), 6.95 (d, J=10, 1H), 5.17 (d, J=5, 1H), 4.75 (s, 1H), 3.7–3.6 (m, 1H), 2.2–1.9 (m, 2H), 1.45–1.3 (m, 1H), 1.15–1.0 (m, 1H).

EXAMPLE 34

Allyl[7S,6R]-7-[[2-(triphenylmethyl)amino-4-thiazolyl](t-butoxy carbonyl methoxyimino) acetyl] amido3-trifluoromethyl-1-carba(1-dethia)-3-cephem-4-carboxylate The titled compound was prepared in a similar fashion to Example 20 yielding 41% of a white solid.

$^1$H NMR(CDCl$_3$): 8.68 (d, 1H), 7.34 (s, 16H), 7.02 (s, 1H), 6.80 (s, 1H), 6.05.9 (m, 1H), 5.57 (dd, 1H), 5.4–5.2

(m, 2H), 4.8–4.7 (m, 4H), 4.0–3.9 (m, 1H), 2.5–2.4 (m, 1H), 2.4–2.3 (m, 1H), 2.2–2.1 (m, 1H), 1.65–1.5 (m, 1H), 1.44 (s, 9H).

EXAMPLE 35

[7S,6R]-7-([2-amino-4-thiazolyl(carboxymethoxyimino)acetyl]-3-trifluoromethyl-1-carba(1-dethia)-3-cephem-4-carboxylic acid 200 mg (0.245 mmoles) of the above product in Example 34 was treated with 2.5 ml cold trifluoroacetic acid and 0.8 ml cold triethylsilate under $N_2$ in an ice bath for one hour. The bath was then removed and the solution was allowed to warm to room temperature and stirred overnight. The solution was diluted with acetonitrile and evaporated to a small volume in vacuo at 30° C., then diluted two more times with acetonitrile and evaporated to dryness. The residue was triturated with diethyl ether and 73 mg of a crude beige solid collected by suction filtration (57%).

65 mg (0.126 mmoles) of the above crude product was dissolved in 3 ml anhydrous acetonitrile under $N_2$ and 3 mg (0.0126 mmoles) triphenylphosphine and 1 mg (0.00252 mmoles) palladium acetate was added. The solution was cooled in an ice bath while 0.036 ml (0.132 mmoles) tributyltin hydride was added via syringe. After one hour, the solution was treated with 0.014 ml (0.252 mmoles) acetic acid and stirred 30 minutes. The precipitate was collected and washed with diethyl ether and then recrystallized from methanol/ethyl acetate/diethyl ether to give 21 mg of a light yellow solid (35% yield).

$^1$H NMR (DMSO-$d_6$): 9.45–9.3 (m, 1H), 7.14 (s, 2H), 6.76 (s, 1H), 5.5–5.4 (m, 1H), 4.56 (s, 2H), 3.9–3.8 (m, 1H), 2.4–2.2 (m, 2H), 1.95–1.85 (m, 1H), 1.6–1.45 (m, 1H).

EXAMPLE 36

Allyl[7S,6R]-7-[D,L-α-(t-butoxycarbonylamino)-3-thienylacetylamino]-3-trifluoromethyl-1-carba(1-dethia)-3-cephem-4-carboxylate The titled compound, prepared in a similar fashion to Example 20, yielded an off-white solid (91%).

EXAMPLE 37

[7S,6R]-7-[D,L-α-(t-butoxycarbonylamino)-3-thienylacetylamino]-3-trifluoromethyl-1-carba(1-dethia)-3-cephem-4-carboxylic acid The titled product was prepared from the product of Example 36 according to the procedure for Example 21 and was not further purified.

EXAMPLE 38

[6R,7S]-7-β-[D-α-(amino)-3-thienylacetylamino]-3-trifluoromethyl-1-carba-1-dethia- b 3-cephem-4-carboxylic acid The titled product was prepared from the crude product of Example 37 via the procedure given for Example 22 and was chromatographed on a C18 column using methanol/acetic acid/$H_2O$ to give 18% product after lyophilization.

$^1$H NMR (DMSO-$d_6$): 9.3–9.2 (m, 1H), 7.6–7.5 (m, 2H), 7.15 (d, 1H), 5.3–5.2 (m, 1H), 4.90 (s, 1H), 3.85–3.6 (m, 1H), 2.2–2.0 (m, 2H), 1.45–1.2 (m, 2H).

EXAMPLE 39

Allyl[7S,6R]-7-β-[D-α-(t-butoxycarbonylamino)-3-benzthienylacetylamino]-3-trifluoromethyl-1-carba(1-dethia)-3-cephem-4-carboxylate The titled compound, prepared in a similar manner to Example 20 yielded a white foam (60%).

EXAMPLE 40

[7S,6R]-7-β-[D-α-(t-butoxycarbonylamino)-3-benzthienylacetylamino]-3-trifluoromethyl-1-carba(1-dethia)-3-cephem-4-carboxylic acid The titled compound was prepared from the product of Example 39 according to the procedure for Example 21 and was not purified.

EXAMPLE 41

[6R,7S]-7-β-[D-α-(amino)-3-benzthienylacetylamino]-3-trifluoromethyl-1-carba(1-dethia)-3-cephem-4-carboxylic acid The titled compound was prepared according to the procedure for Example 22 from the crude product of Example 40 and was chromatographed on a C18 column using methanol/acetic acid/$H_2O$ and lyophilized to give a 32% yield of a white solid.

$^1$H NMR (DMSO-$d_6$): 9.35 (d, 1H), 9.1–8.5 (br s, 3H), 8.1–7.9 (m, 2H), 7.9 (s, 1H), 7.5–7.3 (m, 2H), 5.5–5.3 (m, 2H), 3.9–3.7 (m, 1H), 2.2–2.1 (m, 2H), 1.4–1.3 (m, 1H), 1.2–1.1 (m, 1H).

EXAMPLE 42

Allyl 7-(N-t-butyloxycarbonyl-N-phenoxy acetyl)amino-3-bromo-1-carba(1-dethia)-2,3-cephem-4-carboxylate A 60/40 Δ2/Δ3 mixture of the 3-bromo compound from Preparation 3 (100 mg, 0.2297 mmoles) was combined with DMAP (29 mg, 0.2343 mmoles) and di-t-butyldicarbonate (0.2412 mmol, 85 μl). The mixture was stirred for about 1 hour at room temperature. The mixture was directly chromatographed on silica gel eluting with 20% EtOAc/$CH_2Cl_2$ to afford 104 mg (85% yield) of the titled product as a 60/40 mix of the Δ2/Δ3 isomers, respectively. Data for Δ2 isomer:

$^1$H NMR (300 mHz, $CDCl_3$): δ 7.30 (t, J=8Hz, 2H), 7.0 (t, J=6 Hz, 1H), 6.90 (d, J=8 Hz, 2H), 6.30 (m, 1H), 5.95 (m, 1H), 5.65 (m, 1H), 5.35 (m, 2H), 5.10 (m, 2H), 4.88 (s, 1H), 4.75 (m, 2H), 4.10 (m, 1H), 2.25 (m, 2H), and 1.50 (s, 9H).

EXAMPLE 43

Allyl-7(N-t-butyloxycarbonyl-N-phenoxy acetyl)amino]-3-bromo-1-carba(1-dethia)-2-cephem-4-carboxylate Pure Δ2 isomer of the 3-bromo compound from Preparation 3 (4.6 grams, 10.57 mmoles) was combined with di-t-butyldicarbonate (2.54 grams, 11.6241 mmoles, 2.65 ml), then DMAP (1.33 grams, 10.88 mmoles) and stirred. The mixture was processed as in Example 34 and 5.3 grams (93.6% yield) of the titled product was obtained.

EXAMPLE 44

Allyl[7S,6R]-7-t-butyloxycarbonylamino-3-bromo-1-carba(1-dethia)-2-cephem-4-carboxylate The product from Example 42 (104 mg, 0.1947 mmoles) was combined with THF (2 ml) and a first portion of LiOH (0.1652 ml), and stirred for 40 minutes. After this, a second portion of LiOH was added (0.0295 ml) and the mixture stirred for an hour. The mixture was poured into 40 ml EtOAc and then mixed with 10 ml $H_2O$/10 ml saturated $NaHCO_3$ solution. The organics were separated, dried with $Na_2SO_4$, filtered and concentrated to give 79 mg (> 100% yield) of the crude product. Data for Δ2 isomer:

$^1$H NMR (300 MHz), CDCl$_3$) δ 6.35 (m, 1H), 5.95 (m, 1H), 5.35 (m, 2H), 5.15 (m, 2H), 4.88 (s, 1H), 4.68 (m, 2H), 4.05 (m, 1H), 2.35 (m, 2H), and 1.42 (s, 9H)

EXAMPLE 45

Allyl-[7S,6R]-7-butyloxycarbonylamino-3-bromo-1-carba(1-dethia)-2-cephem-4-carboxylate Product from Example 43 (5.25 grams, 9.8076 mmoles) was combined with THF (95 ml) and a first portion of LiOH (8.75 ml) and stirred for approximately 40 minutes. The second portion of LiOH was added (1.55 ml) and the mixture was stirred for an hour. The mixture was processed as according to Example 36, and resulted in 4.02 grams (> 100% yield) of the titled product.

EXAMPLE 46

Allyl-7S,6R]-7-butyloxycarbonylamino-3-bromo-1-carba(1-dethia)-3-cephem-4-carboxylate (a) The product from Example 44 (16 mg, 0.0399 mmoles) was combined with 0.3 ml of $CH_2Cl_2$, and DBU (0.0064 mmoles, 1.0 μl). The mixture was stirred for 60 minutes at room temperature. The mixture was pipetted through 1 gram of silica, and then eluted with 10% EtOAC/$CH_2Cl_2$.

The titled product passed through and left DBU on silica. The mixture was concentrated to a foam, and resulted in 15.1 mg of product in a ratio of 15/85 of the Δ2/Δ3 isomers, which represents a 94.4% recovery based on a theoretical maximum of 16 mg.

EXAMPLE 47

Allyl-[7S,6R]-7-butyloxycarbonylamino-3-bromo-1-carba(1-dethia)-3-cephem-4-carboxylate The product from Example 45 (4.0 grams, 9.97 mmoles) was processed according to Example 38 except that 6% EtOAc/$CH_2Cl_2$ was used instead of a 10% solution to obtain the pure Δ3 isomer. The following reaction conditions were used:

DBU: 2.5 mmol, 0.373 ml
$CH_2Cl_2$ : 70 ml

The crude mixture was loaded directly onto an 8 inch deep by 4 inch diameter (silica) chromatography column and eluted with 6% EtOAc/$CH_2Cl_2$, resulting in 1.98 grams of the desired Δ3 isomer and 610 mg of a Δ2/Δ3 mixture which was rechromatographed as above to give an additional 250 mg of pure Δ3, and 360 mg of pure Δ2. Pure Δ3 was added to give a total of 2.23 g (66% yield) of pure Δ3 isomer.

$^1$H NMR (300 mHz, CHCl$_3$) δ 5.95 (m, 1H), 5.35 (m, 3H), 5.15 (m, 1H), 4.75 (m, 2H), 3.85 (m, 1H), 2.75 (m, 2H), 2.0 (m, 1H), 1.70 (m, 1H), and 1.42 (s, 9H).

IR (CHCl$_3$) 3019, 1775, 1718, 1504, 1369, 1206, and 1055 cm$^{-1}$.

MS, m/e 400 (M+),

Analysis for: $C_{16}H_{21}N_2 O_5Br$:
Calculated: C, 47.89; H, 5.28; N, 6.78; Br, 19.91 7;
Found C, 47.85; H, 5.05; N, 6.77; Br, 19.76.

EXAMPLE 48

[7S,6R]-7-(aminophenylacetyl)amino-3-bromo-1-carba(1-dethia)-3-cephem-4-carboxylic acid A) In a 25 ml flask, 78 mg (0.1944 mmoles) of allyl[7S,6R]-7-butyloxycarbonylamino-3-bromo-1-carba(1-dethia)-3-cephem-4-carboxylic in 4ml of EtOH and 37 mg (0.1944 mmoles) of p-toluenesulfonic acid monohydrate were added at 30° C. and the mixture was concentrated to dryness. EtOH (4 ml) was added, and the mixture concentrated to dryness again.

In a separate flask 46 mg (0.1944 mmoles) of (2-propenyloxy)carbonylamino-D-phenylglycine and 34 mg (0.1944 moles) of chlorodimethoxytriazine in 1.5 ml $CH_2Cl_2$ were combined and cooled to 0° C. N-methylmorpholine (NMM) was added and the mixture was stirred for 40 minutes. At this time another equivalent of NMM was added, followed by the mixture in the first flask. The mixture was allowed to warm to room temperature for 2-5 hours. The mixture was concentrated to near dryness, and 1 ml CHCl$_2$ and 1 ml of 50/50 EtOACl/hexane were added. The mixture was then loaded onto a 15 g (silica) chromatography column and eluted with 10% MEOH/EtOAC, resulting in 74 mg of allyl-7-(phenyl(2-propenyloxy)carbonylamino)acetylamino-3-bromo-1-carba-(1-dethia)-3-ceph em-4-carboxylate, the physical data of which is shown below.

$^1$HNMR (300 MHz, CDCl$_3$)δ 7.30 (s, 5H), 7.08 (m, 1H), 5.95 (m, 3H), 5.25 (m, 6H), 4.72 (d, J=6Hz, 2H), 4.52 (m, 2H), 3.82 (m, 1H), 2.62 (m, 2H), 1.58 (m, 1H), and 1.25 (m, 1H).

IR (CHCl$_3$) 3019, 1775, 1727, 1689, 1496, 1241, and 1052 cm-1.

MS, m/e 517.

Anal. calculated for $C_{23}H_{24}N_3O_6Br$
Theory: C, 53.29; H, 4.67; N, 8.11; Br, 15.4;
Found: C, 53.51; H, 4.46; N, 7.93; Br, 15.4.

B) In a 25 ml flask, 73 mg (0.1408 mmoles) of the product from part (A) in 2.0 ml of $CH_3CN$ and 1.0 mL of Et$_2$O, 7.4 mg (0.0282 mmoles) of triphenylphosphine, and 1.4 mg (0.0056 mmoles) of palladium acetate were combined. The mixture was cooled to 0° C. after five minutes and 76 μl Bu$_3$SnH was added via microsyringe. The mixture was allowed to warm to room temperature and was stirred for 45 minutes. To the mixture 4 μl of Bu$_3$SnH and 2 ml Et$_2$O were added and allowed to stir an additional 30 minutes. Concentrated HCl (23.5 μl, 12 M) was added to the mixture, at which time precipitation occurred. Ten ml of Et$_2$O was added and the mixture was transferred to a 40 ml centrifuge tube. Thereafter, 20 ml of Et$_2$O was added and the mixture centrifuged. The solid was decanted and washed (2×10 ml CH$_3$CN/10 ml Et$_2$O) then washed twice with 15 ml Et$_2$O. The mixture was dried in a vacuum to produce 51.5 mg of brown solid. The brown solid was dissolved in 1.2 ml of CH$_3$CN and 0.13 ml of 1N HCl, centrifuged, and decanted into a 15 ml centrifuge tube. While swirling, slightly more than 1 equivalent of 1.5 M NH$_4$OH was added to set the pH to about 4.0 at which time a white solid precipitated. The white solid was centrifuged and decanted, and washed once with 8 ml Et₂O and washed twice with 8 ml 1/1 Et₂O/hexane, and thereafter dried to give 46.5 mg of the titled product. The physical data for the titled product is below.

¹HNMR (300 MHz, D₂O) δ 7.55 (m, 5H), 5.40 (d, J=12Hz, 1H), 5.20 (s, 1H), 3.85 (m, 1H), 2.50 (m, 2H), 1.55 (m, 1H), and 1.25 (m, 1H).

IR (KBr) 3150, 3050, 1770, 1750, 1625, 1550, 1405, and 1325 cm⁻¹.

MS, m/e 394 (M+ +1).

EXAMPLE 49

7-(((2-amino-4-thiazolyl)methoxyiminoacetyl)amino)-3-bromo-1-carba(1-dethia)-3-cephem-4-car boxylate acid A) In a 50 ml flask, 240 mg (0.5981 mmoles) of allyl-7-t-butyloxyamino-3-bromo-1-carba(1-dethia)-3-cephem-4-carboxylate in 8 ml of EtOH and 114 mg (0.5981 mmoles) of p-toluenesulfonic acid monohydrate were combined and sonicated until all the solid was dissolved. The mixture was concentrated to dryness, and 8 ml of EtOH was added to the mixture and the mixture was again concentrated to dryness. In a second 50 ml flask, 181 mg (0.5981 mmoles) of [2-(t-butoxycarbonyl)amino-4-thiazolyl(methoxyimino)acetic acid and 105 mg (0.5981 mmoles) of chlorodimethoxytriazine in 4.5 ml CH₂Cl₂ were combined and cooled to 0° C. N-methylmorpholine (NMM) (69 μl, 0.628 mmole) was added to the second flask and the contents were stirred for 45 minutes. After stirring, another equivalent of NMM was added followed by the contents of the first flask in CH₂Cl₂ via pipette. The second flask was allowed to reach room temperature and stirred for 2.5 hours. The mixture was concentrated to near dryness and 2.5 ml CH₂Cl₂/EtOAC was added. Thereafter, the mixture was loaded into a flask chromatography column (50 g, silica), and eluted with a 80/20 CH₂Cl₂/ETOAC. The desired material was concentrated to give 270 mg of the above.

¹HNMR (300 MHz, CDCl₃) δ 9.45 (s, 1H), 8.25 (d, J=8HZ, 1H), 6.98 (s, 1H), 5.95 (m, 1H), 5.68 (m, 1H), 5.35 (m, 2H), 4.75 (m, 2H), 4.0 (m, 1H), 3.95 (s, 3H), 2.80 (m, 2H), 2.10 (m, 1H), 1.90 (m, 1H), and 1.52 (s, 9H).

MS, m/e 583 (m+ +1).

Anal. calculated for C₂₂H₂₅N₅O₇SBr

Theory: C, 45.29: H, 4.32: N, 12.00:

Found: C, 45.09; H, 4.52; N, 11.76.

B) The product from A) (270 mg, 0.4623 mmoles) in 3 ml CH₂Cl₂ was placed in a 50 ml flask with 54 mg (0.5085 mmoles) of sodium ethylhexanoate in 3 ml EtOAC. Into the flask 3.1 mg (0.0116 mmoles) of triphenylphosphine and 13.4 mg (0.0116) of tetrakistriphenylphosphine palladium (0) were placed, and the mixture stirred for 1.5 hours. 30 ml of Et₂O was added to precipitate out the solid, and the mixture was stirred for another 20 minutes, at which time it was poured into 200 ml CH₂Cl₂ and 75 ml 1N HCl. The solid was separated out, dried with Na₂SO₄, filtered, and concentrated to dryness to give 250 mg.

C) In a 50 ml flask, 251 mg (0.4591 mmol) of the product from (B) and 3 ml of CH₂Cl₂ were placed and cooled to 0° C. 0.22 ml (1.38 mmoles) of Et₃SiH was added to the flask, followed by 3 ml of trifluoroacetic acid and the mixture was allowed to warm to room temperature and stirred for 35–40 minutes. The mixture was diluted with 25 ml CH₃CN and concentrated to 1 ml. Three times, 10 ml of CH₃CN and 10 ml of toluene were added and the mixture concentrated to dryness, to give a tan solid. The solid was chromatographed on 75 g (silica) and eluted with 0.5% ACOH/4.5% isopropanol/20% CH₃CN/75% ETOAC, until all the desired solid came off. Desired fractions were concentrated to ½ ml and precipitated out with Et₂O. The mixture was centrifuged and dried to give 60 mg of the titled product. The solid was rechromatographed on 10 g HP20SS, eluting with 0.25% ACOH, 10% CH₃CN, 89.75% H₂O, at 10 ml fractions were collected.

¹HNMR (300 MHz, D₂O) δ 7.08 (s, 1H), 5.46 (d, J=12Hz, 1H), 4.10 (m, 1H), 4.05 (s, 3H), 2.78 (m, 2H), 2.05 (m, 1H), and 1.80 (m, 1H).

MS, m/e 444 (m+ +1).

The compounds of formula (1) inhibit the growth of certain pathogenic organisms as demonstrated by the agar dilution method in which test compounds were diluted to an appropriate range of concentrations in 0.1 M phosphate buffer, pH 7.0, incorporated into Mueller-Hinton agar (Difco), supplemented with 1% Bacto-Supplement C (Difco) at 50° C. and allowed to solidify in petri dishes. Fresh overnight cultures of test bacteria were diluted to approximately 1x(10)4 cells/microliter and applied in one microliter volumes to the surfaces of the agar plates. The innoculated plates were incubated overnight at 35° C. in ambient air. Minimum inhibitory concentration (mic) endpoints were recorded as the lowest antibiotic concentrations in micrograms per milliliter that inhibited the development of visible growth on the plates. The following summarizes the results of such tests with the compounds of the examples listed above.

The following compound numbers are assigned to the compounds for reference in Table 2:

1. 7β-[D-α-(amino)phenylacetylamino]-3-trifluoromethyl-1-carba-(1-dethia)-3-cephem-4-carboxyl ic acid
2. [6R,7S]-7β-[D-α-(amino)-4-hydroxyphenylacetylamino]-3-trifluoromethyl-1-carba-1-dethia-3-cephem-4-carboxylic acid
3. [6R,7S]-7-β-[D-α-(amino)-4-fluorophenylacetylamino]-3-trifluoromethyl-1-carba-1-dethia-3-cephem-4-carboxylic acid
4. [7S,6R]-7-([2-Amino-4-thiazolyl(methoxyimino)acetyl]amido)-3-trifluoromethyl-1-carba( b 1-dethia)-3-cephem-4-carboxylic acid
5. [7S,6R-7-([2-amino-4-thiazolyl(oximino)acetyl]amido)-3-trifluoromethyl-1-carba(1-d ethia)-3-cephem-4-carboxylic acid
6. [6R,7S-7-β-[D-α-(amino)-3-ethylsulfonamidophenylacetylamino]-3-trifluoromethyl-1-carba- b 1-dethia-3-cephem-4-carboxylic acid
7. [6R, 7S]-7-β-[D-α-(amino)-3-bromophenylacetylamino-3-trifluoromethyl-1-carba-1-det hia-3-cephem-4-carboxylic acid
8. [6R,7S]-7-β-[D-α-(amino)-3-fluorophenylacetylamino-3-trifluoromethyl-1-carba-1-det hia-3-cephem-4-carboxylic acid
9. [6R,7S]-7-β-[D-α-(amino)-3-trifluoromethylacetylamino-3-trifluoromethyl-1-carba-1-dethia-3-cephem-4-carboxylic acid

TABLE 2

| | In Vitro Activity of Formula I Compounds | | | | | | | | |
|---|---|---|---|---|---|---|---|---|---|
| | MIC (mcg/ml) | | | | | | | | |
| | Compound Number | | | | | | | | |
| Organism | 1 | 2 | 3 | 4 | 5 | 6 | 7 | 8 | 9 |
| *Staphylococcus aureus* NRRL X1.1 | 2 | 0.85 | 1 | 4 | 1 | 4 | 1 | 2 | 2 |
| *Staphylococcus aureus* V41 | 16 | 7.2 | 16 | 8 | 2 | 8 | 4 | 16 | 4 |
| *Staphylococcus aureus* X400 | 64 | 102 | 64 | 128 | 8 | 32 | 16 | 64 | 16 |
| *Staphylococcus aureus* S13E | 32 | 70.4 | 32 | 16 | 4 | 32 | 8 | 32 | 16 |
| *Staphylococcus epidermidis* EPI270 | 4 | 4.4 | 4 | 8 | 4 | 8 | 1 | 4 | 4 |
| *Staphylococcus epidermidis* 222 | 4 | 2.2 | 4 | 4 | 1 | 4 | 1 | 4 | 1 |
| *Staphylococcus pyogenes* C203 | 0.060 | 0.025 | .06 | — | — | 0.06 | 0.125 | 0.06 | 6 |
| *Staphylococcus pneumoniae* Park 1 | 0.125 | 0.2 | .25 | — | .015 | 0.125 | 0.125 | .25 | .125 |
| *Enterococcus faecium* X66 | 32 | 32 | 32 | >128 | 8 | 64 | 16 | 64 | 32 |
| *Enterococcus faecalis* 2041 | 16 | 22.4 | 32 | 1 | 1 | 32 | 8 | 32 | 16 |
| *Haemophilus influenzae* C.L. | 0.5 | 0.7 | .5 | .015 | .125 | 1 | 0.5 | 2 | 1 |
| *Haemophilus influenzae* 76 | 1.0 | 0.9 | 1 | — | .125 | 4 | 1 | 2 | 1 |
| *Escherichia coli* N10 | 2.0 | 0.85 | 2 | .06 | .125 | 8 | 8 | 4 | 32 |
| *Escherichia coli* EC14 | 0.5 | 0.48 | 1 | .03 | .03 | 1 | 4 | 4 | 8 |
| *Escherichia coli* TEM | 0.5 | 0.75 | 1 | .125 | .03 | 1 | 4 | 2 | 16 |
| *Klebsiella pneumoniae* X26 | 0.25 | 0.3 | .5 | — | .015 | 0.25 | 0.25 | 2 | 1 |
| *Klebsiella pneumoniae* KAE | 8 | 2.3 | 8 | 32 | .06 | 32 | 16 | 16 | 64 |
| *Klebsiella pneumoniae* X68 | 0.5 | 0.6 | 1 | .015 | .06 | 1 | 4 | 2 | 16 |
| *Enterobacter aerogenes* C32 | 4 | 2.08 | 8 | .25 | .25 | 16 | 16 | 16 | 128 |
| *Enterobacter aerogenes* EB17 | 4 | 1.83 | 8 | .125 | .06 | 16 | 32 | 8 | 128 |
| *Enterobacter cloacae* EB5 | 8 | 4.3 | 8 | .25 | .125 | 32 | 64 | 16 | 4 |
| *Enterobacter cloacae* 265A | 16 | 2.3 | 8 | 64 | 16 | 32 | 64 | 32 | 128 |
| Salmonella X514 | .25 | 0.19 | .5 | .015 | .015 | 1 | 4 | 2 | 32 |
| Salmonella 1335 | 1 | 0.58 | 2 | .06 | .06 | 8 | 16 | 4 | 64 |
| Serratia X99 | 8 | 4.7 | 16 | .5 | .5 | 64 | 64 | 32 | 128 |
| Serratia SE3 | 32 | 16 | 32 | 2 | 8 | 128 | >128 | 64 | >128 |
| *Shig sonn.* N9 | 1.0 | 0.58 | 2 | .06 | .06 | 4 | 128 | 2 | 128 |
| *Morg morg* PR15 | 32 | 26.7 | 16 | 4 | 2 | 16 | 16 | 32 | 32 |
| *Proteus incon* PR33 | 16 | 2.3 | 8 | .125 | .25 | 16 | 8 | 16 | 32 |
| *Proteus rett* C24 | 8 | 6.7 | 8 | 1 | .125 | 32 | 128 | 16 | 64 |
| Citro CF17 | 8 | 5.3 | 8 | 8 | 16 | 32 | 32 | 16 | 128 |
| Acom AC12 | 16 | 21.3 | 64 | 16 | 2 | 64 | 16 | 32 | 32 |

We claim:

1. A process for the preparation of a compound of the formula

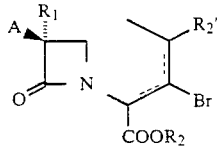

(3)

wherein
- R<sub>1</sub> is hydrogen, $C_1$-$C_4$ alkoxy, $C_1$-$C_4$ alkylthio, or the formamido group NHCHO;
- R<sub>2</sub> is hydrogen or a carboxy-protecting group;
- R<sub>2'</sub> is hydrogen, hydroxy, $C_1$-$C_5$ alkyl, $C_1$-$C_5$ alkyl substituted by halogen, halogen, $C_1$-$C_5$ alkoxy, $C_1$-$C_5$ acyloxy, $C_1$-$C_5$ acyl, $C_1$-$C_5$ alkylthio, or nitrile; and
- A is an amino or a protected amino and when R<sub>2</sub> is hydrogen the pharmaceutically acceptable salts of the acids represented thereby;
which comprises reacting a compound of the formula

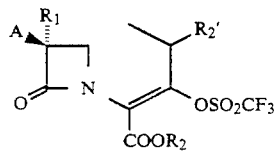

with a bromide containing salt in the presence of a hindered amine base for a time and at a temperature sufficient to produce compound (3).

2. The process as recited in claim 1 wherein A is a group of the formula

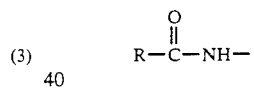

wherein R is hydrogen, $C_1$-$C_6$ alkyl, $C_1$-$C_6$ alkyl substituted by cyano, carboxy, halogen, amino, $C_1$-$C_4$ alkoxy, $C_1$-$C_4$ alkylthio, trifluoromethyl or trifluoromethylthio; naphthyl, phenyl or substituted phenyl group of the formula

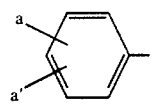

wherein a and a' independently are hydrogen, halogen, cyano, nitro, hydroxy, $C_1$-$C_4$ alkoxy, $C_1$-$C_4$ alkanoyloxy, $C_1$-$C_4$ alkyl, $C_1$-$C_4$ alkylthio, amino, $C_1$-$C_4$ alkanoylamino, $C_1$-$C_4$ alkylsulfonylamino, carboxy, carbamoyl, hydroxymethyl, aminomethyl, or carboxymethyl; a group of the formula

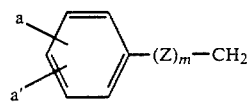

wherein a and a' have the same meanings as defined above, Z is O or S, and m is 0 or 1; an arylmethyl group of the formula

R₃—CH₂— wherein R₃ is naphthyl, thienyl, furyl, benzothienyl, benzoaminothiazolyl, benzofuryl, pyridyl, 4-pyridylthio, pyrimidyl, pyridazinyl, indolyl, imidazolyl, triazolyl, tetrazolyl, oxazolyl, thiazolyl, oxadiazolyl, thiadiazolyl, and said arylmethyl groups substituted by amino, hydroxy, cyano, nitro, halogen, $C_1$-$C_4$ alkyl, $C_1$-$C_4$ alkyoxy, phenyl or substituted phenyl or $C_1$-$C_4$ alkysulfonylamino; a substituted methyl group of the formula

wherein R₄ is cyclohex-1,4-dienyl, a phenyl or substituted phenyl of the formula

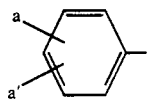

wherein a and a' are as defined above, or R₄ is R₃ as defined above, and Q is hydroxy, $C_1$-$C_4$ alkanoyloxy, carboxy, sulfo, amino, sulfoamino, or a substituted amino group of the formula

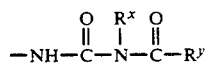

wherein $R^x$ is hydrogen or $C_1$-$C_3$ alkyl, $R^y$ is $C_1$-$C_4$ alkyl, furyl, thienyl, phenyl, halophenyl, nitrophenyl, styryl, halostyryl, nitrostyryl or a group of the formula

wherein $R^x$ has the same meanings as defined above and $R^z$ is hydrogen, $C_1$-$C_3$ alkylsulfonyl, $C_1$-$C_3$ alkyl, or $C_1$-$C_4$ alkanoyl; or Q is a substituted amino group of the formula

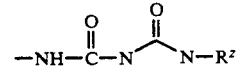

(CH₂)q wherein $R^z$ has the same meaning as defined above, and q is 2 or 3; or Q is a substituted amino group of the formula

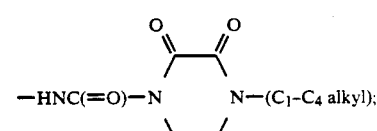

or Q is a benzamido group of the formula

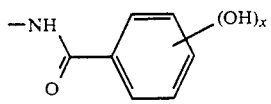

wherein x if 1 to 3; or Q is a hydroxy-substituted pyridonyl-carbonylamino group of the formula

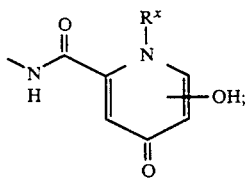

wherein $R^x$ is as defined above;
or Q is a pyridylcarbonylamino group of the formula

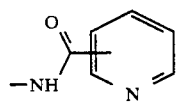

said group optionally substituted by $C_1$-$C_4$ alkyl, amino, carboxy, hydroxy or halogen;
or Q is an imidazolyl or pyrazolyl group of the formula

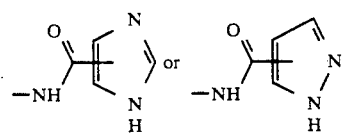

and said imidazolyl or pyrazolyl optionally substituted by $C_1$-$C_4$ alkyl, carboxy, amino or halogen; or Q is a benzpyridazin-4-one group or tautomer thereof represented by the formula

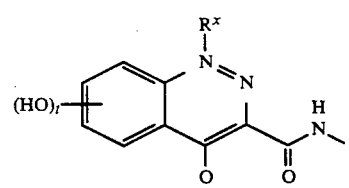

or

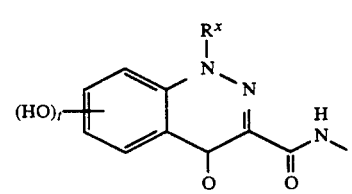

wherein $R^x$ is as defined above, and t is 1 to 3; or Q is a benzpyranone group of the formula

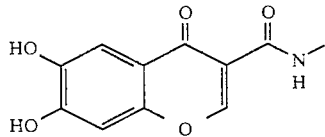

or R is a group of the formula

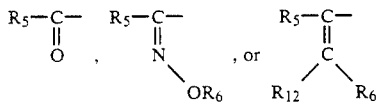

wherein $R_5$ is $R_3$ or $R_4$ as defined above, $R_{12}$ is hydrogen or halogen, and $R_6$ is hydrogen, $C_1$-$C_4$ alkyl, $C_1$-$C_4$ alkyl substituted by halogen, a carboxy-substituted alkyl or cycloalkyl group represented by the formula

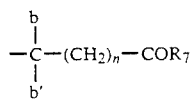

wherein b and b' independently are hydrogen or $C_1$-$C_3$ alkyl, n is 0, 1, 2, or 3; and b and b' when taken together with the carbon to which they are bonded form a 3- to 6-membered carbocyclic ring, and $R_7$ is hydroxy, $C_1$-$C_4$ amino, $C_1$-$C_4$ alkylamino, or di($C_1$-$C_4$ alkyl)amino; or $R_6$ is $C_1$-$C_4$ substituted by phenyl or phenyl substituted by one or two of the same or different groups selected from among $C_1$-$C_4$ alkyl, hydroxy, halogen, carboxy or protected carboxy; or $R_6$ is $C_1$-$C_4$ alkyl substituted by amino or protected amino; or $R_6$ is $C_1$-$C_4$ alkenyl; or $R_6$ is a cyclic lactam group of the formula

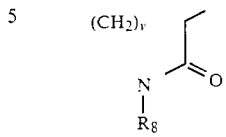

wherein v is 2–4 and $R_8$ is hydrogen or $C_1$-$C_3$ alkyl; or $R_6$ is an aryl methyl group of the formula $$R_3-CH_2-$$

wherein $R_3$ has the same meaning as defined hereinabove.

3. The process as recited in claim 1 wherein the hindered amine base is 2,6-lutidine.

4. The process as recited in claim 1 wherein the bromide containing salt is LiBr.

5. The process as recited in claim 1 wherein A is phenoxyacetylamino.

6. The process as recited in claim 1 wherein the steps take place at a temperature between about 21° and to about 70° C.

7. The process as recited in claim 6 wherein the temperature is about 65° C.

8. The process as recited in claim 1 further including the step of converting Δ2 isomer of compound (3) to the Δ3 isomer by exposing the Δ2 isomer to a strong base.

9. The process as recited in claim 8 wherein the strong base is 1,8-diazobicycloundec7-ene or 1,5-diazobicyclonon-5-ene.

UNITED STATES PATENT AND TRADEMARK OFFICE
CERTIFICATE OF CORRECTION

PATENT NO. : 5,099,015

DATED : March 24, 1992

INVENTOR(S) : William J. Hornback; John E. Munroe

It is certified that error appears in the above-identified patent and that said Letters Patent is hereby corrected as shown below:

I) The general structure of 1-carba(1-dethia)cephalosporins is

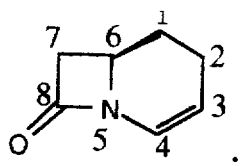

The bond between the 1 and the 6 positions,

needs to be inserted in the structures at the following positions of the patent:

Column 11, lines 50-57;
Column 11, lines 58-65;
Column 12, lines 50-57;
Column 12, lines 58-65;
Column 13, lines 1-13;
Column 14, lines 1-13;
Column 15, lines 1-13;
Column 15, lines 14-19;
Column 15, lines 30-36;
Column 15, lines 37-45;
Column 15, lines 46-54;
Column 16, lines 1-13;
Column 16, lines 14-19;
Column 16, lines 30-36;
Column 16, lines 37-45;

UNITED STATES PATENT AND TRADEMARK OFFICE
CERTIFICATE OF CORRECTION

PATENT NO. : 5,099,015

DATED : March 24, 1992

INVENTOR(S) : William J. Hornback; John E. Munroe

It is certified that error appears in the above-identified patent and that said Letters Patent is hereby corrected as shown below:

(continued from page 1)

Column 17, lines 19-28;
    Column 17, lines 29-35;
    Column 18, lines 19-28;
    Column 18, lines 29-35;
    Column 19, lines 19-26;
    Column 19, lines 49-57;
    Column 20, lines 1-10;
    Column 20, lines 13-20;
    Column 20, lines 40-48;
    Column 20, lines 49-57;
    Column 21, lines 22-30;
    Column 21, lines 32-41;
    Column 21, lines 51-58;
    Column 22, lines 1-8;
    Column 43, lines 39-45; and
    Column 43, lines 58-65.

II) In Column 16, lines 46-54

" 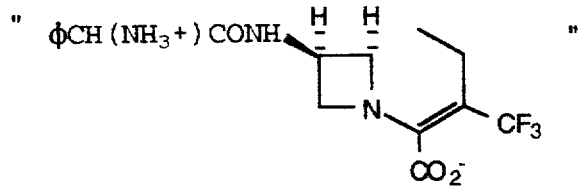 " should read

UNITED STATES PATENT AND TRADEMARK OFFICE
CERTIFICATE OF CORRECTION

PATENT NO. : 5,099,015

DATED : March 24, 1992

INVENTOR(S) : William J. Hornback; John E. Munroe

It is certified that error appears in the above-identified patent and that said Letters Patent is hereby corrected as shown below:

(continued from page 2)

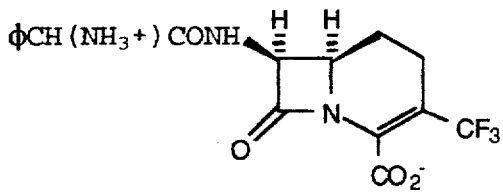

III) Column 45, lines 50-55

" 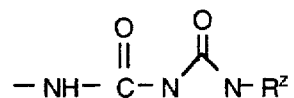 "    should read

-- 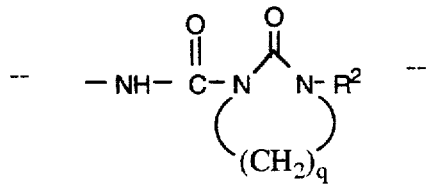 --

UNITED STATES PATENT AND TRADEMARK OFFICE
CERTIFICATE OF CORRECTION

PATENT NO. : 5,099,015
DATED : March 24, 1992
INVENTOR(S) : William J. Hornback; John E. Munroe It is certified that error appears in the above-identified patent and that said Letters Patent is hereby corrected as shown below:

(continued from page 3)

IV) Column 48, lines 5-10

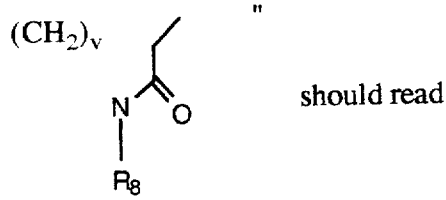   should read

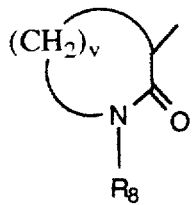

Signed and Sealed this

Twenty-ninth Day of June, 1993

*Attest:*

MICHAEL K. KIRK

*Attesting Officer*   Acting Commissioner of Patents and Trademarks